US009249121B2

(12) United States Patent
Muller et al.

(10) Patent No.: US 9,249,121 B2
(45) Date of Patent: Feb. 2, 2016

(54) SOLID FORMS OF 3-(5-AMINO-2-METHYL-4-OXO-4H-QUINAZOLIN-3-YL)-PIPERIDINE-2,6-DIONE, AND THEIR PHARMACEUTICAL COMPOSITIONS AND USES

(71) Applicant: CELGENE CORPORATION, Summit, NJ (US)

(72) Inventors: George W. Muller, Rancho Santa Fe, CA (US); Hon-Wah Man, Princeton, NJ (US); Benjamin M. Cohen, Cranford, NJ (US); Ying Li, Springfield, NJ (US); Jean Xu, Warren, NJ (US); William W. Leong, Westfield, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/317,912

(22) Filed: Jun. 27, 2014

(65) Prior Publication Data
US 2014/0378484 A1    Dec. 25, 2014

Related U.S. Application Data

(63) Continuation of application No. 13/417,055, filed on Mar. 9, 2012, now Pat. No. 8,802,685.

(60) Provisional application No. 61/451,806, filed on Mar. 11, 2011.

(51) Int. Cl.
C07D 401/04        (2006.01)

(52) U.S. Cl.
CPC .................................... *C07D 401/04* (2013.01)

(58) Field of Classification Search
CPC ........................................................ A61K 31/517
USPC ........................................ 514/266.2; 544/287
See application file for complete search history.

(56) References Cited

U.S. PATENT DOCUMENTS

| | | | |
|---|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,810,643 A | 3/1989 | Souza |
| 4,994,443 A | 2/1991 | Folkman |
| 4,999,291 A | 3/1991 | Souza |
| 5,001,116 A | 3/1991 | Folkman |
| 5,059,595 A | 10/1991 | Le Grazie |
| 5,073,543 A | 12/1991 | Marshall |
| 5,120,548 A | 6/1992 | Mc Clelland |
| 5,134,127 A | 7/1992 | Stella |
| 5,229,496 A | 7/1993 | Deeley |
| 5,354,556 A | 10/1994 | Sparks |
| 5,391,485 A | 2/1995 | Deeley |
| 5,393,870 A | 2/1995 | Deeley |
| 5,528,823 A | 6/1996 | Rudy, Jr. |
| 5,580,755 A | 12/1996 | Souza |
| 5,591,767 A | 1/1997 | Mohr |
| 5,632,984 A | 5/1997 | Wong |
| 5,635,517 A | 6/1997 | Muller |
| 5,639,476 A | 6/1997 | Oshlack |
| 5,674,533 A | 10/1997 | Santus |
| 5,733,566 A | 3/1998 | Lewis |
| 5,770,589 A | 6/1998 | Billson |
| 5,800,819 A | 9/1998 | Wambebe |
| 6,001,368 A | 12/1999 | Jenks |
| 6,015,803 A | 1/2000 | Wirostko |
| 6,218,369 B1 | 4/2001 | Bombardelli |
| 6,225,348 B1 | 5/2001 | Paulsen |
| 6,281,230 B1 | 8/2001 | Muller |
| 7,182,953 B2 | 2/2007 | Zeldis |
| 7,189,740 B2 | 3/2007 | Zeldis |
| 7,393,862 B2 | 7/2008 | Zeldis |
| 7,563,810 B2 | 7/2009 | Zeldis |
| 7,635,700 B2 | 12/2009 | Muller |
| 7,968,569 B2 | 6/2011 | Zeldis |
| 2003/0133939 A1 | 7/2003 | Ledbetter |
| 2004/0087546 A1 | 5/2004 | Zeldis |
| 2004/0091455 A1 | 5/2004 | Zeldis |
| 2004/0190609 A1 | 9/2004 | Watanabe |
| 2004/0220144 A1 | 11/2004 | Zeldis |
| 2005/0100529 A1 | 5/2005 | Zeldis |
| 2005/0143344 A1 | 6/2005 | Zeldis et al. |
| 2005/0143420 A1 | 6/2005 | Moutouh-de Parseval |
| 2005/0203142 A1 | 9/2005 | Zeldis et al. |
| 2005/0214328 A1 | 9/2005 | Zeldis |
| 2005/0222209 A1 | 10/2005 | Zeldis |
| 2005/0238646 A1 | 10/2005 | Ledbetter |
| 2005/0239842 A1 | 10/2005 | Zeldis |
| 2006/0122228 A1 | 6/2006 | Zeldis |

(Continued)

FOREIGN PATENT DOCUMENTS

| | | |
|---|---|---|
| EP | 0688771 | 12/1995 |
| GB | 768821 | 2/1957 |
| WO | WO 95/01348 | 1/1995 |
| WO | WO 01/43743 | 6/2001 |
| WO | WO 02/32925 | 4/2002 |
| WO | WO 02/059106 | 8/2002 |
| WO | WO 02/064083 | 8/2002 |
| WO | WO 02/070480 | 9/2002 |
| WO | WO 02/088171 | 11/2002 |
| WO | WO 2004/103274 | 12/2004 |
| WO | WO 2005/023192 | 3/2005 |
| WO | WO 2005/037989 | 4/2005 |
| WO | WO 2006/055689 | 5/2006 |
| WO | WO 2008/039489 | 4/2008 |
| WO | WO 2009/042177 | 4/2009 |
| WO | WO 2009/042200 | 4/2009 |
| WO | WO 2011/034504 | 3/2011 |

OTHER PUBLICATIONS

Vippagunta et al (2001).*

(Continued)

*Primary Examiner* — Paul V Ward
(74) *Attorney, Agent, or Firm* — Jones Day

(57) ABSTRACT

Solid forms comprising 3-(5-amino-2-methyl-4-oxo-4H-quinazolin-3-yl)-piperidine-2,6-dione, compositions comprising the solid forms, methods of making the solid forms and methods of their uses are disclosed.

53 Claims, 24 Drawing Sheets

(56) References Cited

U.S. PATENT DOCUMENTS

| | | |
|---|---|---|
| 2006/0154880 A1 | 7/2006 | Hensel |
| 2006/0188475 A1 | 8/2006 | Xu |
| 2008/0051379 A1 | 2/2008 | Lerner |
| 2012/0230983 A1 | 9/2012 | Muller et al. |

OTHER PUBLICATIONS

McMahon et al (2000).*
Pinedo et al (2000).*
Cancer Drug Design and Discovery, Neidle, Stephen, ed. (Elsevier/Academic Press, 2008).*
Aklilu et al., Annals of Oncology 15:1109-1114 (2004).
Angers et al., Nature, 443:590-593 (2006).
Anolik et al., Clinical Immunology, 122:2:139-145 (2007).
Byrn et al., Solid State Chemistry of Drugs, SSCI, West Lafayette (1999).
Caira, "Crystalline Polymorphism of Organic Compounds," Topics in Current Chemistry, Springer, Berlin, Germany, 198:163-208 (1998).
Cairns et al., Nature Rev., 11:85-95 (2011).
Cancer: Principles & Practice of Oncology (3rd Edition) pp. 1843-1847 (1989).
Carstensen, Drug Stability: Principles & Practice, 2d. Ed., Marcel Dekker, NY, NY, pp. 379-380 (1995).
Cerny et al., Ann Oncol 13 Suppl4:211-216 (2002).
Chemburkar et al., Org. Process Res. Dev. 4:413-417 (2000).
Emens et al., Curr. Opinion Mol. Ther. 3(1):77-84 (2001).
Folkman et al., Science 221:719-725 (1983).
Higgins et al., Neurology, 63:1927-1931 (2004).
Hohberger et al., FEES Lett, 583:633-637 (2009).
Ito et al., Science, 327:1345-1350 (2010).
Jemal, et al., CA Cancer J Clin 57(1):43-66 (2007).
Jo et al., J. Neurochem, 94:1212-1224 (2005).
Kim et al., Journal of Clinical Oncology, ASCO Annual Meeting Proceedings Part I., 25(18S), Jun. 20 Supplement, p. 8082 (2007).
Mardis et al., N. Engl. J. Med., 361: 1058-1066 (2009).
Parsons et al., Science 321:1807-1812 (2008).
Penichet et al, J. Immunol. Methods 248:91-101 (2001).
Response Evaluation Criteria in Solid Tumors (RECIST) Guidelines, Journal of the National Cancer Institute 92(3): 205-216 (2000).
Roitt et al., Immunology, 17.1-17.12, 3rd ed., Mosby, St. Louis, Mo. (1993).
Shackelford, D.B. & Shaw, R.J., Nature Rev. Cancer, 9: 563-575 (2009).
Taylor et al., Nature 297:307 (1982).
The Merck Manual, 944-952, 17th ed. (1999).
The United States Pharmacopeia, 23rd ed., 1843-1844 (1995).
Vippagunta et al., Adv. Drug. Deliv. Rev., 48:3-26 (2001).
Wilen et al., Tetrahedron 33:2725 (1977).
Wilen, Tables of Resolving 5 Agents and Optical Resolutions, p. 268, E.L. Eliel, Ed., Univ. of Notre Dame Press, Notre Dame, IN (1972).
Yu, Adv. Drug. Deliv. Rev., 48:27-42 (2001).
Index Merck 14 th. Merck & Co. NJ. USA. 2006. No.- 0009255 (Thalidomide).

* cited by examiner

TABLE 1

SOLID FORMS OF 3-(5-AMINO-2-METHYL-4-OXO-4H-QUINAZOLIN-3-YL)-PIPERIDINE-2,6-DIONE, AND THEIR PHARMACEUTICAL COMPOSITIONS AND USES

The present application is a continuation of U.S. patent application Ser. No. 13/417,055, filed Mar. 9, 2012, now pending, which claims priority to U.S. Provisional Patent Application No. 61/451,806, filed Mar. 11, 2011, the entirety of which is incorporated herein by reference.

1. FIELD

Provided herein are solid forms of 3-(5-amino-2-methyl-4-oxo-4H-quinazolin-3-yl)-piperidine-2,6-dione, pharmaceutical compositions thereof, and methods of their uses for the treatment of diseases or disorders.

2. BACKGROUND OF THE DISCLOSURE

2.1 Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples include cancers of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to, diabetic retinopathy, retinopathy of prematurity, corneal graft rejection, neovascular glaucoma, retrolental fibroplasia, arthritis, and proliferative vitreoretinopathy.

Accordingly, compounds that can control angiogenesis or inhibit the production of certain cytokines, including TNFα, may be useful in the treatment and prevention of various diseases and conditions.

2.2 Methods of Treating Cancer

Current cancer therapy may involve surgery, chemotherapy, hormonal therapy and/or radiation treatment to eradicate neoplastic cells in a patient (see, e.g., Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there is a variety of chemotherapeutic agents available for treatment of cancer. A majority of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., Goodman and Gilman's: *The Pharmacological Basis of Therapeutics*, Tenth Ed. (McGraw Hill, N.Y.).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443.

Still, there is a significant need for safe and effective methods of treating, preventing and managing cancer and other diseases and conditions, including for diseases that are refractory to standard treatments, such as surgery, radiation therapy, chemotherapy and hormonal therapy, while reducing or avoiding the toxicities and/or side effects associated with the conventional therapies.

2.3 Solid Forms

The preparation and selection of a solid form of a pharmaceutical compound is complex, given that a change in solid form may affect a variety of physical and chemical properties, which may provide benefits or drawbacks in processing, formulation, stability and bioavailability, among other important pharmaceutical characteristics. Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, potential solid forms of a pharmaceutical compound include single-component and multiple-component solids. Single-component solids consist essentially of the pharmaceutical compound in the absence of other compounds. Variety among single-component crystalline materials may potentially arise, e.g., from the phenomenon of polymorphism, wherein multiple three-dimensional arrangements exist for a particular pharmaceutical compound (see, e.g., S. R. Byrn et al., Solid State Chemistry of Drugs, (1999) SSCI, West Lafayette). The importance of studying polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Additional diversity among the potential solid forms of a pharmaceutical compound may arise, e.g., from the possibility of multiple-component solids. Crystalline solids comprising two or more ionic species may be termed salts (see, e.g., Handbook of Pharmaceutical Salts Properties, Selection and Use, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., Solid State Chemistry of Drugs, (1999) SSCI, West Lafayette). Moreover, multiple-component crystal forms may potentially be susceptible to polymorphism, wherein a given multiple-component composition may exist in more than one three-dimensional crystalline arrangement. The preparation of solid forms is of great importance in the development of a safe, effective, stable and marketable pharmaceutical compound.

Provided herein are embodiments addressing a need for solid forms of 3-(5-amino-2-methyl-4-oxo-4H-quinazolin-3-yl)-piperidine-2,6-dione ("Compound A"). Compound A was described in U.S. Pat. No. 7,635,700, the disclosure of which is incorporated herein by reference in its entirety.

3. SUMMARY

This disclosure relates to methods of treating diseases and disorders utilizing a solid form of 3-(5-amino-2-methyl-4-oxo-4H-quinazolin-3-yl)-piperidine-2,6-dione or a stereoisomer thereof, or a pharmaceutically acceptable salt, solvate, hydrate, co-crystal, clathrate, or polymorph thereof.

Provided herein are solid forms of 3-(5-amino-2-methyl-4-oxo-4H-quinazolin-3-yl)-piperidine-2,6-dione or a stereoisomer thereof, or a pharmaceutically acceptable salt, solvate, hydrate, co-crystal, clathrate, or polymorph thereof. In one embodiment, the solid form is crystalline Form A. In another embodiment, the solid form is crystalline Form B. In yet another embodiment, the solid form is crystalline Form C. In yet another embodiment, the solid form is Form D. In yet another embodiment, the solid form is crystalline Form E. In yet another embodiment, the solid form is crystalline Form F. In yet another embodiment, the solid form is a solid form of a hydrochloride salt of 3-(5-amino-2-methyl-4-oxo-4H-quinazolin-3-yl)-piperidine-2,6-dione. In still another embodiment, the solid form is crystalline Form A1.

Further provided herein are pharmaceutical compositions, single unit dosage forms, dosing regimens, and kits, which comprise a solid form of 3-(5-amino-2-methyl-4-oxo-4H-quinazolin-3-yl)-piperidine-2,6-dione or a stereoisomer thereof, or a pharmaceutically acceptable salt, solvate, hydrate, co-crystal, clathrate, or polymorph thereof and a pharmaceutically acceptable carrier.

Additionally provided herein are methods of treating and managing various diseases or disorders, which comprise administering to a patient a therapeutically effective amount of a solid form of 3-(5-amino-2-methyl-4-oxo-4H-quinazolin-3-yl)-piperidine-2,6-dione or a stereoisomer thereof, or a pharmaceutically acceptable salt, solvate, hydrate, co-crystal, clathrate, or polymorph thereof.

Also provided herein are methods of preventing various diseases and disorders, which comprise administering to a patient a prophylactically effective amount of a solid form of 3-(5-amino-2-methyl-4-oxo-4H-quinazolin-3-yl)-piperidine-2,6-dione or a stereoisomer thereof, or a pharmaceutically acceptable salt, solvate, hydrate, co-crystal, clathrate, or polymorph thereof.

In certain embodiments, the solid forms are single-component crystal forms of 3-(5-amino-2-methyl-4-oxo-4H-quinazolin-3-yl)-piperidine-2,6-dione. In certain embodiments, the solid forms are multiple-component crystal forms of 3-(5-amino-2-methyl-4-oxo-4H-quinazolin-3-yl)-piperidine-2,6-dione, including, but not limited to, salts, co-crystals and/or solvates (including hydrates) comprising 3-(5-amino-2-methyl-4-oxo-4H-quinazolin-3-yl)-piperidine-2,6-dione. In certain embodiments, the solid forms are single-component amorphous forms of 3-(5-amino-2-methyl-4-oxo-4H-quinazolin-3-yl)-piperidine-2,6-dione. In certain embodiments, the solid forms are multiple-component amorphous forms of 3-(5-amino-2-methyl-4-oxo-4H-quinazolin-3-yl)-piperidine-2,6-dione. Without intending to be limited by any particular theory, certain solid forms provided herein have particular advantageous physical and/or chemical properties making them useful, e.g., for manufacturing, processing, formulation and/or storage, while also possessing particularly advantageous biological properties, such as, e.g., bioavailability and/or biological activity.

In certain embodiments, solid forms provided herein include solid forms comprising 3-(5-amino-2-methyl-4-oxo-4H-quinazolin-3-yl)-piperidine-2,6-dione, including, but not limited to, single-component and multiple-component solid forms comprising 3-(5-amino-2-methyl-4-oxo-4H-quinazolin-3-yl)-piperidine-2,6-dione. In certain embodiments, solid forms provided herein include salts, polymorphs, solvates (including hydrates), and co-crystals comprising 3-(5-amino-2-methyl-4-oxo-4H-quinazolin-3-yl)-piperidine-2,6-dione. Certain embodiments herein provide methods of making, isolating and/or characterizing the solid forms provided herein.

The solid forms provided herein are useful as active pharmaceutical ingredients for the preparation of formulations for use in patients. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, a multiple-component crystal form, a single-component amorphous form and/or a multiple-component amorphous form comprising 3-(5-amino-2-methyl-4-oxo-4H-quinazolin-3-yl)-piperidine-2,6-dione and a pharmaceutically acceptable diluent, excipient or carrier. The solid forms and the final drug products provided herein are useful, for example, for the treatment, prevention or management of diseases and disorders provided herein.

3.1. BRIEF DESCRIPTION OF THE FIGURES

FIG. 1 provides an X-ray Powder Diffraction ("XRPD") pattern of Form A of 3-(5-amino-2-methyl-4-oxo-4H-quinazolin-3-yl)-piperidine-2,6-dione.

FIG. 2 provides a Differential Scanning calorimetry ("DSC") plot of Form A of 3-(5-amino-2-methyl-4-oxo-4H-quinazolin-3-yl)-piperidine-2,6-dione.

FIG. 3 provides a Thermal Gravimetric Analysis ("TGA") plot of Form A of 3-(5-amino-2-methyl-4-oxo-4H-quinazolin-3-yl)-piperidine-2,6-dione.

FIG. 4 provides an XRPD pattern of Form B of 3-(5-amino-2-methyl-4-oxo-4H-quinazolin-3-yl)-piperidine-2,6-dione.

FIG. 5 provides a DSC plot of Form B of 3-(5-amino-2-methyl-4-oxo-4H-quinazolin-3-yl)-piperidine-2,6-dione.

FIG. 6 provides a TGA plot of Form B of 3-(5-amino-2-methyl-4-oxo-4H-quinazolin-3-yl)-piperidine-2,6-dione.

FIG. 7 provides an XRPD pattern of Form C of 3-(5-amino-2-methyl-4-oxo-4H-quinazolin-3-yl)-piperidine-2,6-dione.

FIG. 8 provides a DSC plot of Form C of 3-(5-amino-2-methyl-4-oxo-4H-quinazolin-3-yl)-piperidine-2,6-dione.

FIG. 9 provides a TGA plot of Form C of 3-(5-amino-2-methyl-4-oxo-4H-quinazolin-3-yl)-piperidine-2,6-dione.

FIG. 10 provides an XRPD pattern of Form D of 3-(5-amino-2-methyl-4-oxo-4H-quinazolin-3-yl)-piperidine-2,6-dione.

FIG. 11 provides a DSC plot of Form D of 3-(5-amino-2-methyl-4-oxo-4H-quinazolin-3-yl)-piperidine-2,6-dione.

FIG. 12 provides a TGA plot of Form D of 3-(5-amino-2-methyl-4-oxo-4H-quinazolin-3-yl)-piperidine-2,6-dione.

FIG. 13 provides an XRPD pattern of Form E of 3-(5-amino-2-methyl-4-oxo-4H-quinazolin-3-yl)-piperidine-2,6-dione.

FIG. 14 provides a DSC plot of Form E of 3-(5-amino-2-methyl-4-oxo-4H-quinazolin-3-yl)-piperidine-2,6-dione.

FIG. 15 provides a TGA plot of Form E of 3-(5-amino-2-methyl-4-oxo-4H-quinazolin-3-yl)-piperidine-2,6-dione.

FIG. 16 provides an XRPD pattern of Form F of 3-(5-amino-2-methyl-4-oxo-4H-quinazolin-3-yl)-piperidine-2,6-dione.

FIG. 17 provides a DSC plot of Form F of 3-(5-amino-2-methyl-4-oxo-4H-quinazolin-3-yl)-piperidine-2,6-dione.

FIG. 18 provides an XRPD pattern of Form A1 of 3-(5-amino-2-methyl-4-oxo-4H-quinazolin-3-yl)-piperidine-2,6-dione hydrochloride.

FIG. 19 provides a DSC plot of Form A1 of 3-(5-amino-2-methyl-4-oxo-4H-quinazolin-3-yl)-piperidine-2,6-dione hydrochloride.

FIG. 20 provides a TGA plot of Form A1 of 3-(5-amino-2-methyl-4-oxo-4H-quinazolin-3-yl)-piperidine-2,6-dione hydrochloride.

FIG. 21 provides a Dynamic Vapor Sorption ("DVS") plot of Form A1 of 3-(5-amino-2-methyl-4-oxo-4H-quinazolin-3-yl)-piperidine-2,6-dione hydrochloride.

3.2. DEFINITIONS

Figure 1:
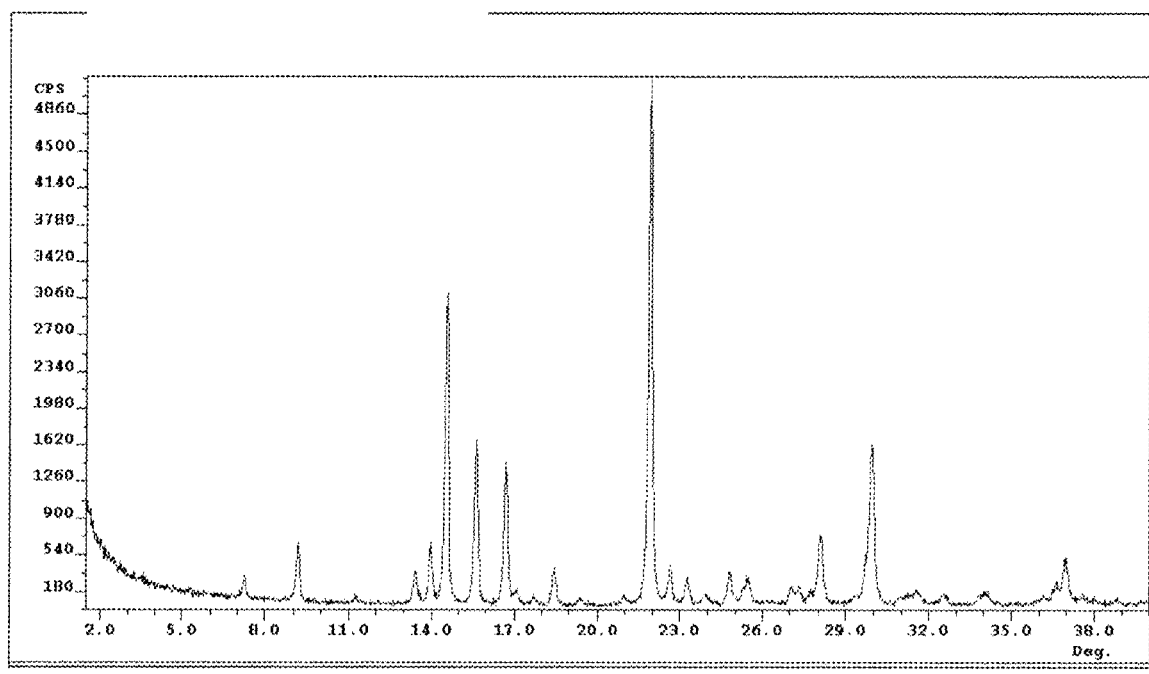

As used herein, term "Compound A" refers to 3-(5-amino-2-methyl-4-oxo-4H-quinazolin-3-yl)-piperidine-2,6-dione. The $^1$H NMR spectrum of Compound A is substantially as follows: δ (DMSO-$d_6$): 2.10-2.17 (m, 1H), 2.53 (s, 3H), 2.59-2.69 (m, 2H), 2.76-2.89 (m, 1H), 5.14 (dd, J=6, 11 Hz, 1H), 6.56 (d, J=8 Hz, 1H), 6.59 (d, J=8 Hz, 1H), 7.02 (s, 2H), 7.36 (t, J=8 Hz, 1H), 10.98 (s, 1H). The $^{13}$C NMR spectrum of Compound A is substantially as follows: δ (DMSO-$d_6$): 20.98, 23.14, 30.52, 55.92, 104.15, 110.48, 111.37, 134.92, 148.17, 150.55, 153.62, 162.59, 169.65, 172.57.

Without being limited by theory, Compound A is believed to be 3-(5-amino-2-methyl-4-oxo-4H-quinazolin-3-yl)-piperidine-2,6-dione, which has the following structure:

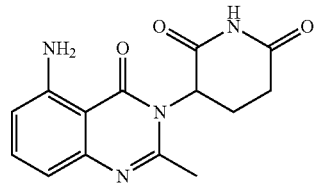 [SMILES: Cc1nc2cccc(N)c2c(=O)n1C1CCC(=O)NC1=O]

As used herein, the term "patient" refers to a mammal, particularly a human.

As used herein, the term "pharmaceutically acceptable salt" refers to a salt prepared from a pharmaceutically acceptable non-toxic acid or base, including inorganic acids and bases and organic acids and bases.

As used herein, term "adverse effects" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes, but is not limited to, gastric and intestinal ulcerations and erosions. The term "renal toxicities" includes, but is not limited to, such conditions as papillary necrosis and chronic interstitial nephritis.

As used herein and unless otherwise indicated, the phrases "reduce or avoid adverse effects" and "reducing or avoiding adverse effects" mean the reduction of the severity of one or more adverse effects as defined herein.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

As used herein and unless otherwise specified, the terms "solid form" and related terms refer to a physical form which is not predominantly in a liquid or a gaseous state. As used herein and unless otherwise specified, the term "solid form" and related terms, when used herein to refer to Compound A, refer to a physical form comprising Compound A which is not predominantly in a liquid or a gaseous state. Solid forms may be crystalline, amorphous, or mixtures thereof. In particular embodiments, solid forms may be liquid crystals. A "single-component" solid form comprising Compound A consists essentially of Compound A. A "multiple-component" solid form comprising Compound A comprises a significant quantity of one or more additional species, such as ions and/or molecules, within the solid form. In certain embodiments, a "multiple-component" solid form comprising Compound A comprises a hydrochloride salt of compound A. For example, in particular embodiments, a crystalline multiple-component solid form comprising Compound A further comprises one or more species non-covalently bonded at regular positions in the crystal lattice. Multiple-component solid forms comprising Compound A include co-crystals, solvates (e.g., hydrates), and clathrates of Compound A. In particular embodiments, the term "solid form comprising Compound A" and related terms include single-component and multiple-component solid forms comprising Compound A. In particular embodiments, "solid forms comprising Compound A" and related terms include crystal forms comprising Compound A, amorphous forms comprising Compound A, and mixtures thereof.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21$^{st}$ edition, Lippincott, Williams and Wilkins, Baltimore, Md. (2005); The United States Pharmacopeia, 23$^{rd}$ ed., 1843-1844 (1995).

As used herein and unless otherwise specified, the term "crystal forms," "crystalline forms" and related terms herein refer to solid forms that are crystalline. Crystal forms include single-component crystal forms and multiple-component crystal forms, and include, but are not limited to, salts (e.g., a hydrochloride salt), polymorphs, solvates, hydrates, and/or other molecular complexes. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

As used herein and unless otherwise specified, the terms "polymorphs," "polymorphic forms" and related terms herein, refer to two or more crystal forms that consist essentially of the same molecule, molecules, and/or ions. Like different crystal forms, different polymorphs may have different physical properties such as, e.g., melting temperature, heat of fusion, solubility, dissolution properties and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (e.g., one polymorph might be more likely to form solvates or might be difficult to filter and wash free of impurities, and particle shape and size distribution might be different between polymorphs).

As used herein and unless otherwise specified, the terms "solvate" and "solvated," refer to a crystal form of a substance which contains solvent. The terms "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance be about 99%, 98%, 97%, 96%, 95%, 94%, 93%, 92%, 91% or 90% physically and/or chemically pure.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis, and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context and unless otherwise specified, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values.

As used herein and unless otherwise specified, a sample comprising a particular crystal form or amorphous form that is "substantially pure," e.g., substantially free of other solid forms and/or of other chemical compounds, contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

As used herein and unless otherwise specified, a sample or composition that is "substantially free" of one or more other solid forms and/or other chemical compounds means that the composition contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or other chemical compounds.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the diluent, excipient or carrier must be compatible with the other ingredients of the formulation and not deleterious to the recipient thereof.

4. DETAILED DESCRIPTION

This disclosure relates to solid forms of Compound A, which is 3-(5-amino-2-methyl-4-oxo-4H-quinazolin-3-yl)-piperidine-2,6-dione, and stereoisomers thereof, and pharmaceutically acceptable salts, solvates, hydrates, co-crystals, clathrates, and polymorphs thereof; as well as methods of using, and compositions comprising, a solid form of Compound A or a stereoisomer thereof, or a pharmaceutically acceptable salt, solvate, hydrate, co-crystal, clathrate, or polymorph thereof. For example, the present disclosure encompasses the in vitro and in vivo use of a solid form of Compound A, and the incorporation of a solid form of Compound A into pharmaceutical compositions and single unit dosage forms useful in the treatment and prevention of a variety of diseases and disorders.

4.1. Solid Forms of Compound A

In one embodiment, provided herein are solid forms of Compound A or a stereoisomer thereof, or a pharmaceutically acceptable salt, solvate, hydrate, co-crystal, clathrate, or polymorph thereof.

Compound A is readily prepared using the methods as described in U.S. Pat. No. 7,635,700, the disclosure of which is incorporated herein by reference in its entirety.

Solid forms comprising Compound A include single-component and multiple-component forms, including crystal forms and amorphous forms, and including, but not limited to, salts, polymorphs, solvates, hydrates, co-crystals and clathrates. Particular embodiments herein provide single-component amorphous solid forms of Compound A. Particular embodiments herein provide single-component crystalline solid forms of Compound A. Particular embodiments herein provide multiple-component amorphous forms comprising Compound A. Particular embodiments herein provide multiple-component crystalline solid forms comprising Compound A. Multiple-component solid forms provided herein include solid forms which may be described by the terms salt, co-crystal, hydrate, solvate, clathrate and/or polymorph, and include solid forms which may be described by one or more of these terms.

Solid forms comprising Compound A can be prepared by the methods described herein, including the methods described in the Examples below, or by techniques known in the art, including heating, cooling, freeze drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding, solvent-drop grinding or liquid assisted grinding), microwave-induced precipitation, sonication-induced precipitation, laser-induced precipitation and precipitation from a supercritical fluid. The particle size of the resulting solid forms, which can vary, (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing or sonication.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

Certain embodiments herein provide compositions comprising one or more of the solid forms. Certain embodiments provide compositions of one or more solid forms in combination with other active ingredients. Certain embodiments provide methods of using these compositions in the treatment, prevention or management of diseases and disorders including, but not limited to, the diseases and disorders provided herein.

Solid forms provided herein may also comprise unnatural proportions of atomic isotopes at one or more of the atoms in Compound A. For example, the compound may be radiolabeled with radioactive isotopes, such as for example tritium ($^3$H), iodine-125 ($^{125}$I) sulfur-35 ($^{35}$S), or carbon-14 ($^{14}$C). Radiolabeled compounds are useful as therapeutic agents, e.g., cancer therapeutic agents, research reagents, e.g., binding assay reagents, and diagnostic agents, e.g., in vivo imaging agents. All isotopic variations of Compound A, whether radioactive or not, are intended to be encompassed within the scope of the embodiments provided herein.

4.1.1. Form A of Compound A

Figure 24:
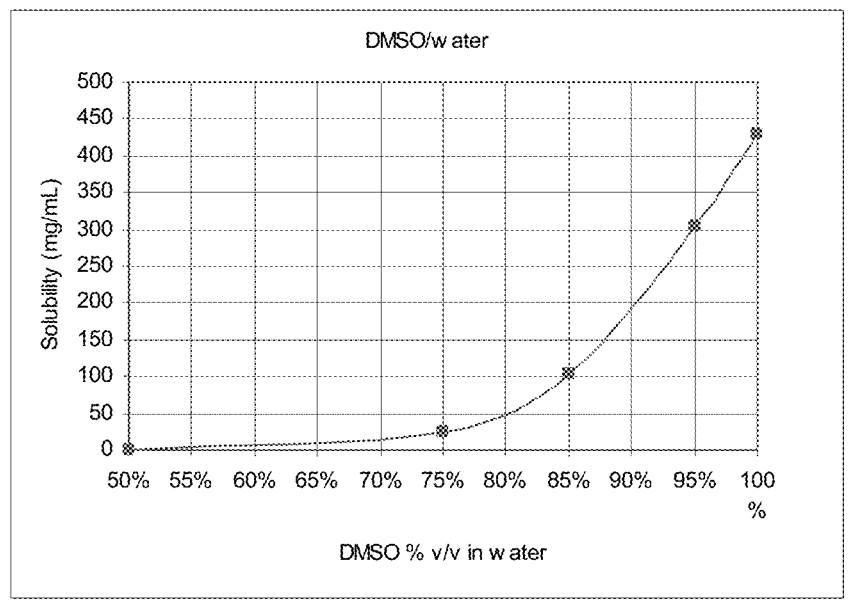
FIG. 24 depicts the solubility of Form A of Compound A in DMSO:water.

Certain embodiments herein provide crystalline Form A of Compound A. Form A may be crystallized from DMSO:water at room temperature, dissolving Compound A in 95:5 DMSO:water (v:v) and crystallizing by adding water to reach 50:50 DMSO:water (v:v). A wide screen of solvents resulted in the selection of DMSO:water, with water being the anti-solvent. Table 1 (FIG. 24) shows the solubility of Form A in DMSO:water as the relative amount of DMSO is increased.

In certain embodiments, Form A of Compound A may be characterized by X-ray powder diffraction analysis. A representative XRPD pattern of Form A of Compound A is provided in FIG. 1. In certain embodiments, Form A of Compound A is characterized by XRPD peaks located at one, two, three, four, five, six, seven, eight, nine, ten, eleven, twelve, or thirteen of the following approximate positions: 9.2, 13.4, 14.0, 14.6, 15.6, 16.7, 18.5, 21.9, 22.7, 24.8, 28.1, 30.0 and 37.0 degrees 2θ. In one embodiment, the Form A of Compound A is characterized by XRPD peaks located at the following approximate positions: 14.6, 15.6, 16.7, 21.9 and 30.0, degrees 2θ. In certain embodiments, Form A of Compound A is characterized by an XRPD pattern which matches the pattern exhibited in FIG. 1. In certain embodiments, Form A of Compound A is characterized by an XRPD pattern having 1, 2, 3, 4, 5, 6, 7, 8, 9, 10, 11, 12 or 13 peaks matching peaks in the representative Form A pattern provided herein.

Figure 2:
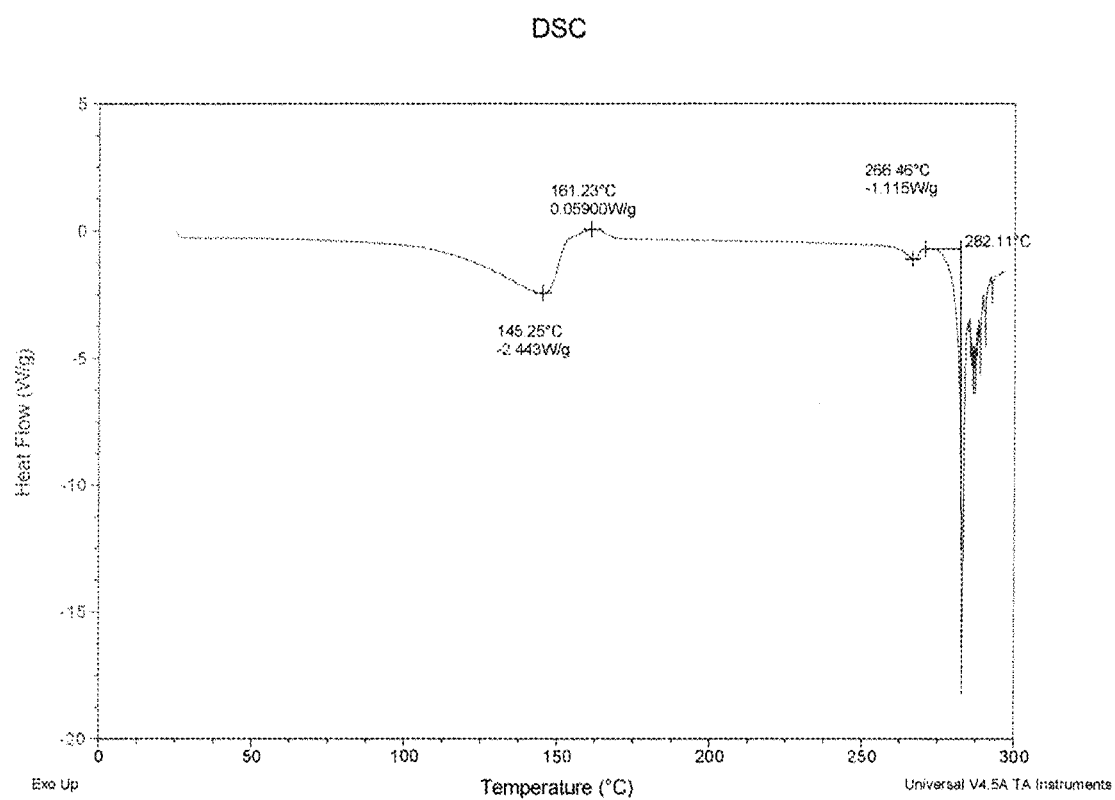
Figure 3:
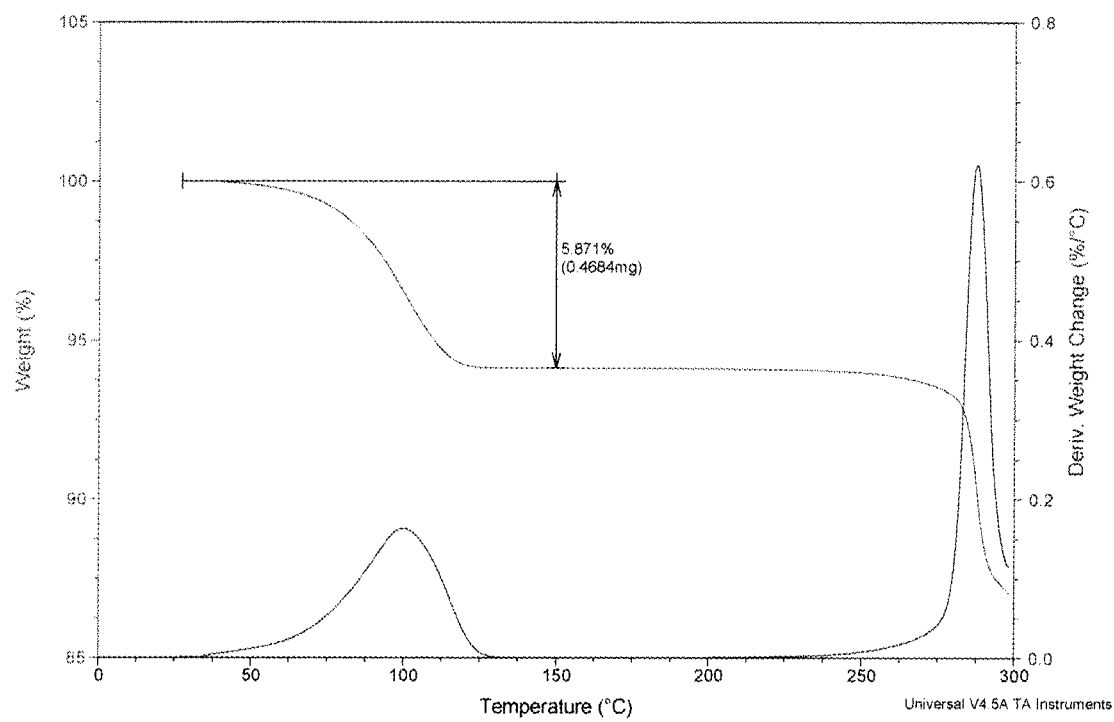

In certain embodiments, Form A of Compound A may be characterized by thermal analysis. A representative DSC plot for Form A of Compound A is shown in FIG. 2. In certain embodiments, Form A is characterized by a DSC plot comprising an endothermic event with an onset temperature of about 282° C. In certain embodiments, a characteristic Form A DSC plot further comprises one or more additional events, such as, e.g., an endothermic event with a peak temperature of about 145° C., and/or an exothermic event with a peak temperature of about 161° C. A representative TGA plot for Form A of Compound A is shown in FIG. 3. In certain embodiments, Form A is characterized by a TGA plot comprising a mass loss of less than about 10%, less than about 8%, or less than about 6%, e.g., about 5.9%, of the total mass of the sample upon heating from about 40° C. to about 110° C. In one embodiment, Form A is characterized by a TGA plot comprising a mass loss of about 5 to about 6% of the total mass of the sample upon heating from about 40° C. to about 110° C. In certain embodiments, Form A of Compound A contains either water or other solvent in the crystal lattice. In certain embodiments, the TGA mass loss event comprises the loss of water. In certain embodiments, Form A is solvated. In certain embodiments, Form A is monohydrated. In certain embodiments, the crystal lattice of Form A comprises about one molar equivalent of water per mole of Compound A.

In certain embodiments, upon dehydration Form A is converted to Form D of Compound A. In one embodiment, Form A is converted to Form D of Compound A when dried at about 55° C. for 3 days. Form A of Compound A may be prepared from Form D by slurrying Form D in water at 22° C. or 50° C. overnight.

In one embodiment, Form A of Compound A is physically and chemically stable at 40° C. for 5 days under vacuum. In another embodiment, Form A of Compound A is physically and chemically stable at 40° C. for 4 days under nitrogen atmosphere.

In certain embodiments, Form A of Compound A may be characterized by moisture sorption analysis. In certain embodiments, when the relative humidity ("RH") is increased from about 0% to about 95% RH, Form A exhibits a mass change ranging from about 1% to about 10%, from about 2 to about 5%, or from about 3 to about 4% of the starting mass of the sample. In certain embodiments, mass gained upon adsorption is lost when the RH is decreased back to about 0% RH.

Certain embodiments herein provide Form A of Compound A which is substantially pure. Certain embodiments herein provide Form A of Compound A which is substantially free of other solid forms comprising Compound A including, e.g., Forms B, C, D, E, and F and/or an amorphous solid form comprising Compound A as provided herein, and Form A1 and an amorphous solid form comprising Compound A hydrochloride as provided herein. Certain embodiments herein provide Form A as a mixture of solid forms comprising Compound A, including, e.g., a mixture comprising one or more of the following: Forms B, C, D, E, F, and an amorphous solid form comprising Compound A as provided herein, and Form A1 and an amorphous solid form comprising Compound A hydrochloride as provided herein.

4.1.2. Form B of Compound A

Certain embodiments herein provide crystalline Form B of Compound A. In certain embodiments, Form B of Compound A can be obtained from various solvents, including, but not limited to, solvent systems comprising acetone, acetonitrile, methanol, and mixtures thereof. In certain embodiments, Form B can be obtained using a slurry recrystallization process. In certain embodiments, Form B is obtained using a slurry recrystallization process in acetone, acetonitrile, methanol, or mixtures thereof at about 50° C.

In certain embodiments, Form B of Compound A may be characterized by X-ray powder diffraction analysis. A representative XRPD pattern of Form B of Compound A is provided in FIG. 4. In certain embodiments, Form B of Compound A is characterized by XRPD peaks located at one, two, three, four, five, six, seven, eight, nine, ten, eleven, twelve, thirteen, fourteen, fifteen or sixteen of the following approximate positions: 10.6, 11.4, 12.6, 13.7, 14.7, 19.1, 20.3, 20.9, 21.2, 22.9, 24.9, 25.3, 25.9, 26.9, 29.5 and 33.8 degrees 2θ. In one embodiment, Form B of Compound A is characterized by XRPD peaks located at the following approximate positions: 10.6, 14.7, 19.1 and 25.9 degrees 2θ. In certain embodiments, Form B of Compound A is characterized by an XRPD pattern which matches the pattern exhibited in FIG. 4. In certain embodiments, Form B of Compound A is characterized by an XRPD pattern having 1, 2, 3, 4, 5, 6, 7, 8, 9, 10, 11, 12, 13, 14, 15 or 16 peaks matching peaks in the representative Form B pattern provided herein.

Figure 5:
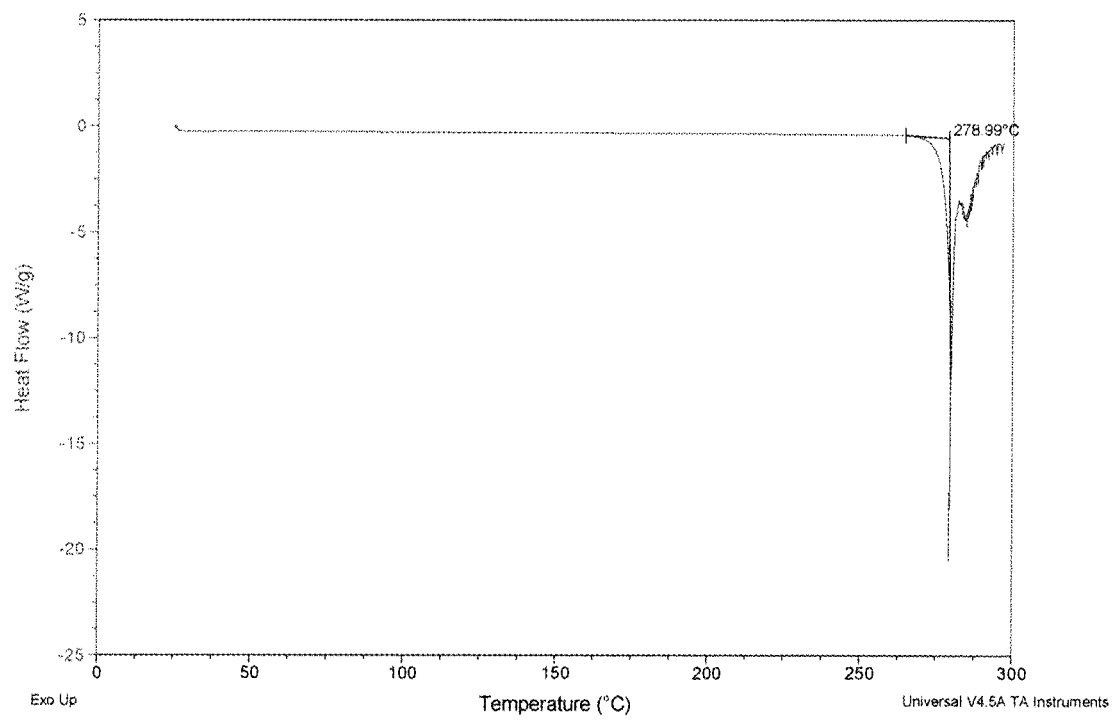
Figure 6:
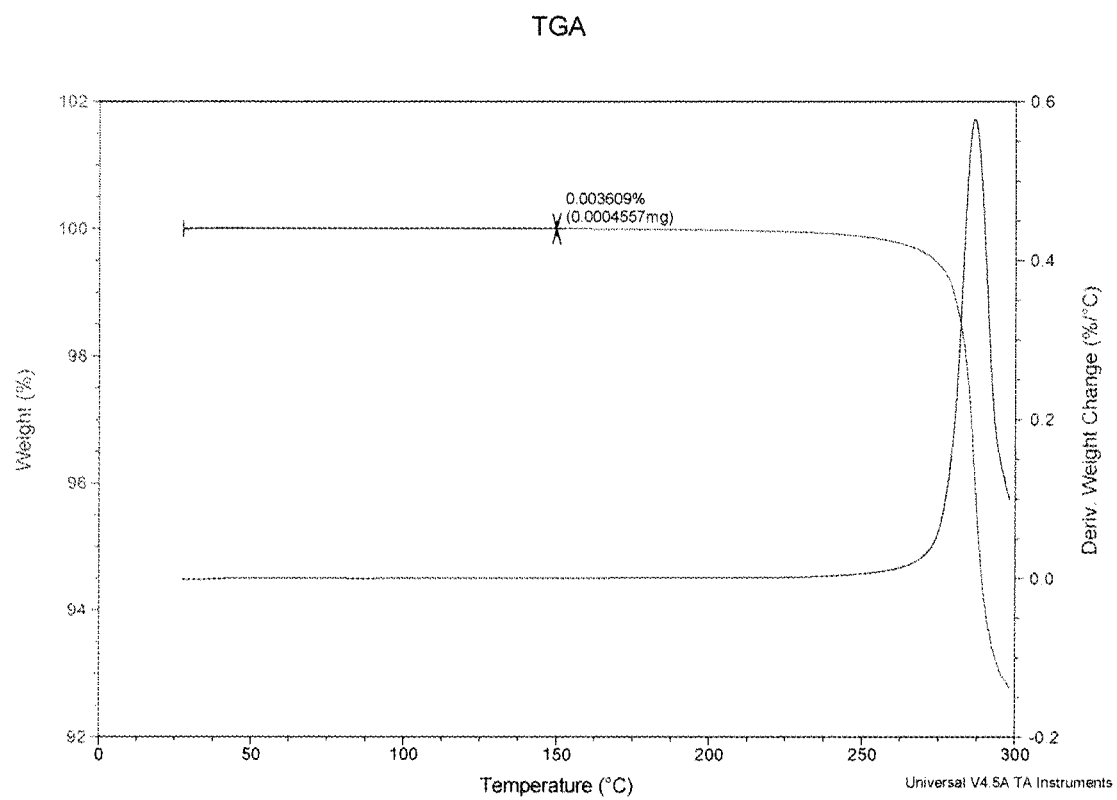

In certain embodiments, Form B of Compound A may be characterized by thermal analysis. A representative DSC plot for Form B of Compound A is shown in FIG. 5. In certain embodiments, Form B is characterized by a DSC plot comprising an endothermic event with an onset temperature of about 279° C. A representative TGA plot for Form B of Compound A is shown in FIG. 6. In certain embodiments, Form B is characterized by a TGA plot comprising a mass loss of less than about 1%, less than about 0.5%, less than about 0.1%, or less than 0.05% of the total mass of the sample upon heating from about 25° C. to about 200° C. In certain embodiments, Form B of Compound A does not contain substantial amounts of either water or other solvent in the crystal lattice. In certain embodiments, Form B is anhydrous. In certain embodiments, Form B is unsolvated.

In certain embodiments, Form B of Compound A may be characterized by moisture sorption analysis. In certain embodiments, when the RH is increased from about 0% to about 95% RH, Form B exhibits a mass change of less than about 1%, less than about 0.5%, or less than about 0.2%, e.g., about 0.1%, of the starting mass of the sample. In certain embodiments, mass gained upon adsorption is lost when the RH is decreased back to about 0% RH. In certain embodiments, Form B is substantially nonhygroscopic. In certain embodiments, the XRPD pattern of Form B material is substantially unchanged following the adsorption/desorption analysis. In certain embodiments, Form B is stable with respect to humidity.

Certain embodiments herein provide Form B of Compound A which is substantially pure. Certain embodiments herein provide Form B of Compound A which is substantially free of other solid forms comprising Compound A including, e.g., Forms A, C, D, E, F, and/or an amorphous solid form comprising Compound A as provided herein, and Form A1 and an amorphous solid form comprising Compound A hydrochloride as provided herein. Certain embodiments herein provide Form B as a mixture of solid forms comprising Compound A, including, e.g., a mixture comprising one or more of the following: Forms A, C, D, E, F, and an amorphous solid form comprising Compound A as provided herein, and Form A1 and an amorphous solid form comprising Compound A hydrochloride as provided herein.

4.1.3. Form C of Compound A

Certain embodiments herein provide crystalline Form C of Compound A. In certain embodiments, Form C of Compound A can be obtained from various solvents, including, but not limited to, solvent systems comprising ethyl acetate, ethanol, 2-propanol, methyl ethyl ketone, n-butanol, tetrahydrofuran, and mixtures comprising two or more thereof. In certain embodiments, Form C can be obtained using a slurry recrystallization process. In certain embodiments, Form C is obtained using a slurry recrystallization process in ethyl acetate, ethanol, 2-propanol, methyl ethyl ketone, n-butanol, tetrahydrofuran, or mixtures comprising two or more thereof, at about 50° C.

In certain embodiments, Form C of Compound A may be characterized by X-ray powder diffraction analysis. A representative XRPD pattern of Form C of Compound A is provided in FIG. 7. In certain embodiments, Form C of Compound A is characterized by XRPD peaks located at one, two, three, four, five, six, seven, eight, nine, ten or eleven of the following approximate positions: 10.8, 11.9, 15.1, 18.8, 19.2, 19.3, 22.0, 24.9, 25.1, 26.6 and 29.2 degrees 2θ. In one embodiment, Form C of Compound A is characterized by XRPD peaks located at the following approximate positions: 10.8, 15.1, 25.1 and 26.6 degrees 2θ. In certain embodiments, Form C of Compound A is characterized by an XRPD pattern which matches the pattern exhibited in FIG. 7. In certain embodiments, Form C of Compound A is characterized by an XRPD pattern having 1, 2, 3, 4, 5, 6, 7, 8, 9, 10 or 11 peaks matching peaks in the representative Form C pattern provided herein.

Figure 8:
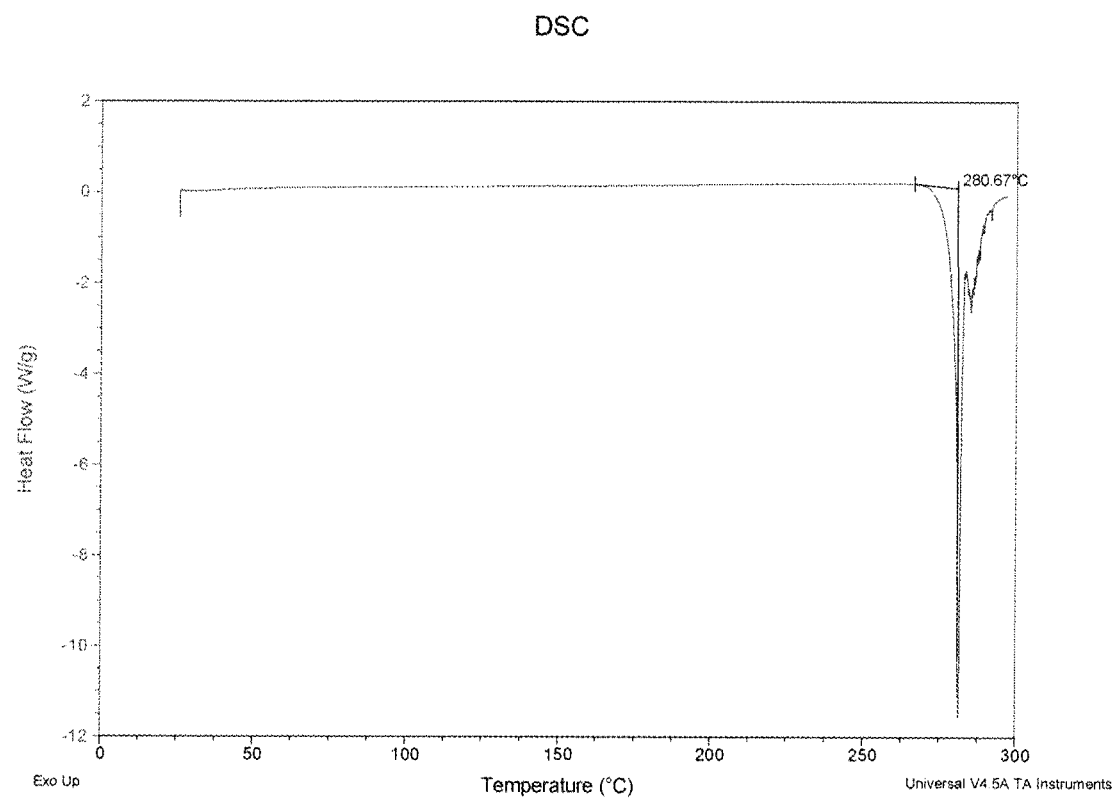
Figure 9:
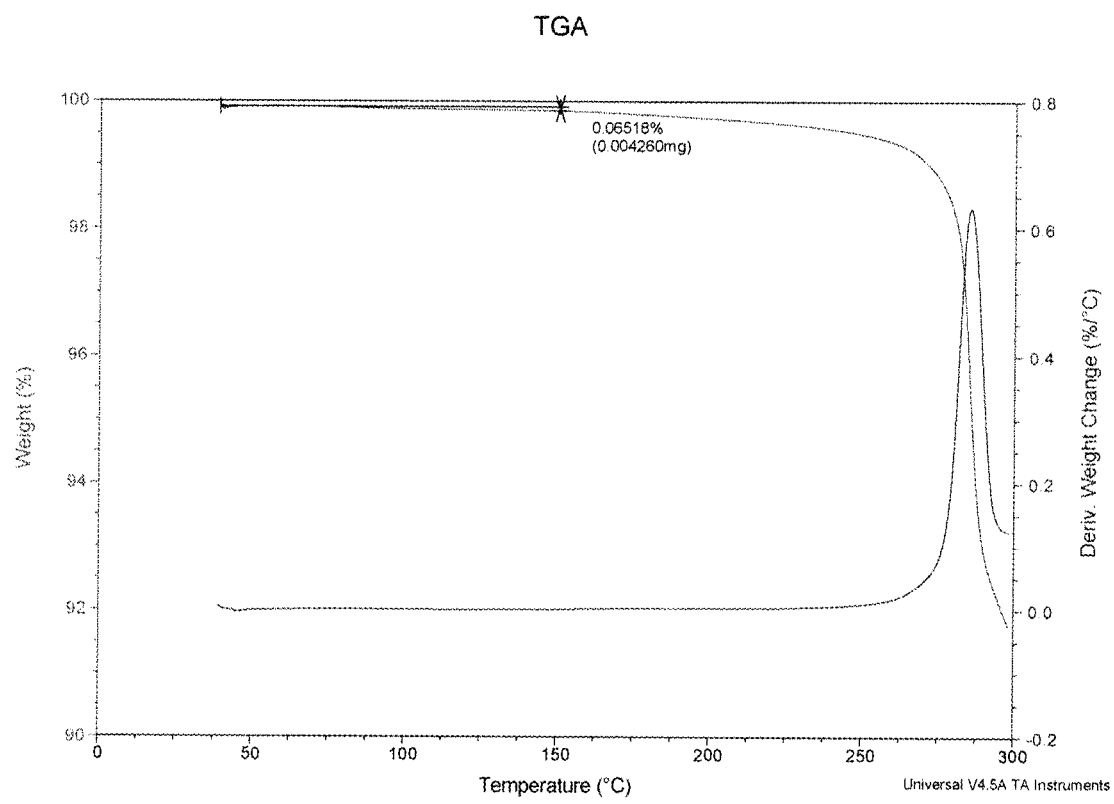

In certain embodiments, Form C of Compound A may be characterized by thermal analysis. A representative DSC plot for Form C of Compound A is shown in FIG. 8. In certain embodiments, Form C is characterized by a DSC plot comprising an endothermic event with an onset temperature of about 281° C. A representative TGA plot for Form C of Compound A is shown in FIG. 9. In certain embodiments, Form C is characterized by a TGA plot comprising a mass loss of less than about 1%, less than about 0.5%, or less than about 0.1%, e.g., about 0.07%, of the total mass of the sample upon heating from about 25° C. to about 150° C. In certain embodiments, Form C of Compound A does not contain substantial amounts of either water or other solvent in the crystal lattice. In certain embodiments, Form C is anhydrous. In certain embodiments, Form C is unsolvated.

In certain embodiments, Form C of Compound A may be characterized by moisture sorption analysis. In certain embodiments, when the RH is increased from about 0% to about 95% RH, Form C exhibits a mass change of less than about 1%, less than about 0.5%, or less than about 0.2%, e.g., about 0.17%, of the starting mass of the sample. In certain embodiments, mass gained upon adsorption is lost when the RH is decreased back to about 0% RH. In certain embodiments, Form C is substantially nonhygroscopic. In certain embodiments, the XRPD pattern of Form C material is substantially unchanged following the adsorption/desorption analysis. In certain embodiments, Form C is stable with respect to humidity.

Certain embodiments herein provide Form C of Compound A which is substantially pure. Certain embodiments herein provide Form C of Compound A which is substantially free of other solid forms comprising Compound A including, e.g., Forms A, B, D, E, F, and/or an amorphous solid form comprising Compound A as provided herein, and Form A1 and an amorphous solid form comprising Compound A hydrochloride as provided herein. Certain embodiments herein provide Form C as a mixture of solid forms comprising Compound A, including, e.g., a mixture comprising one or more of the following: Forms A, B, D, E, F, and an amorphous solid form comprising Compound A as provided herein, and Form A1 and an amorphous solid form comprising Compound A hydrochloride as provided herein.

4.1.4. Form D of Compound A

Certain embodiments herein provide Form D of Compound A. In certain embodiments, Form D of Compound A can be obtained by drying Form A of Compound A in an oven. In certain embodiments, Form D is obtained by drying Form A in an oven at about 70° C.

In certain embodiments, Form D of Compound A may be characterized by X-ray powder diffraction analysis. A representative XRPD pattern of Form D of Compound A is provided in FIG. 10. In certain embodiments, Form D of Compound A is characterized by an XRPD pattern which matches the pattern exhibited in FIG. 10. In certain embodiments, Form D of Compound A is characterized by XRPD peaks located at one, two, three, four, five, six, seven, eight, nine, ten, eleven, twelve, thirteen or fourteen of the following approximate positions: 10.6, 14.0, 14.6, 15.7, 16.3, 16.7, 18.8, 21.7, 21.9, 24.8, 25.1, 25.8, 28.1 and 28.6 degrees 2θ. In one embodiment, Form D of Compound A is characterized by XRPD peaks located at the following approximate positions: 16.7, 21.7, 21.9 and 25.8 degrees 2θ. In certain embodiments, Form D of Compound A is characterized by an XRPD pattern having 1, 2, 3, 4, 5, 6, 7, 8, 9, 10, 11, 12, 13 or 14 peaks matching peaks in the representative Form D pattern provided herein.

Figure 11:
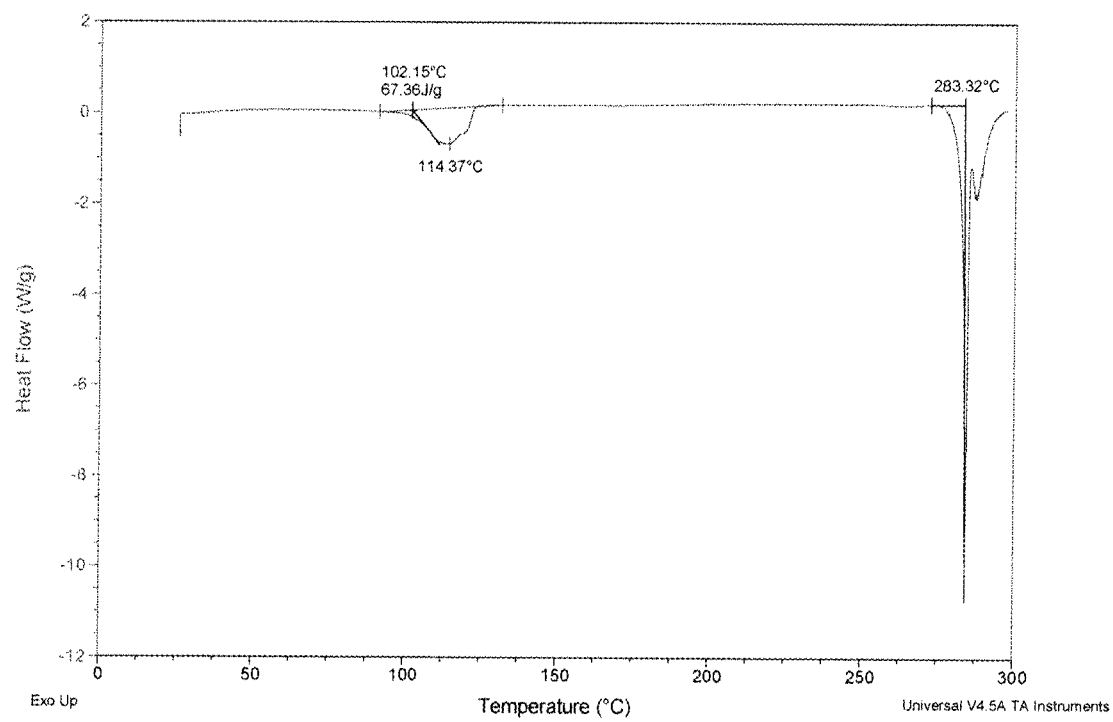
Figure 12:
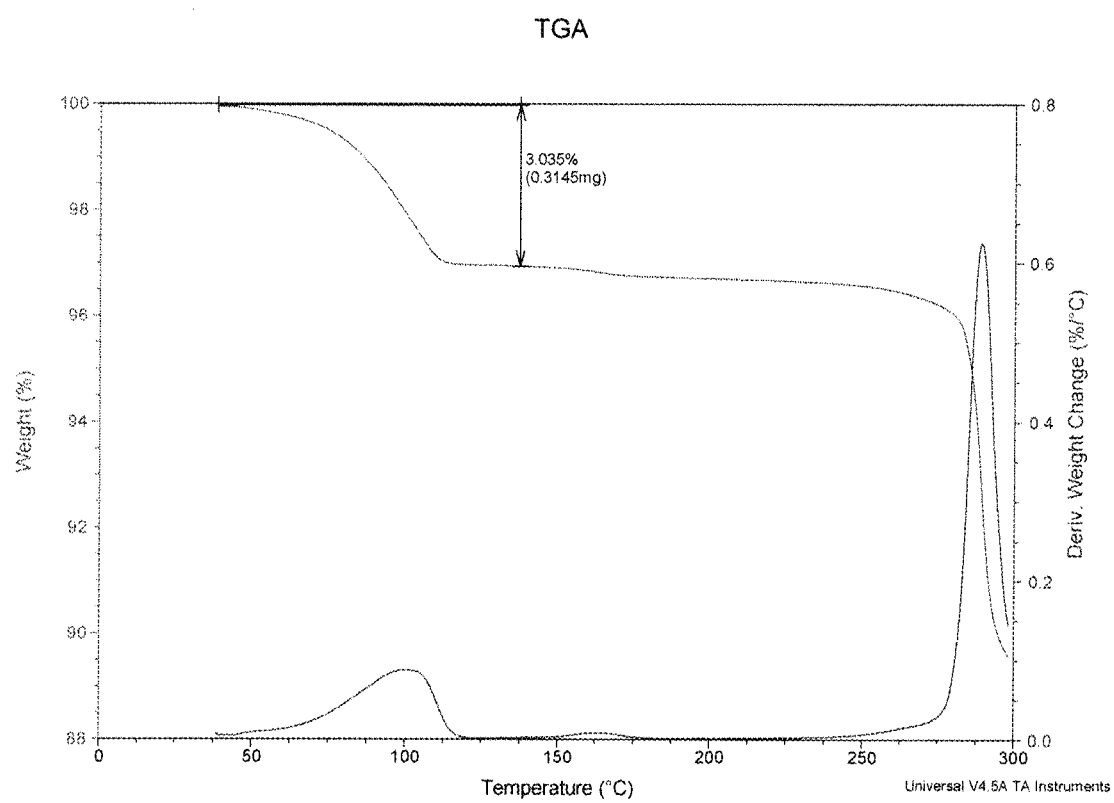

In certain embodiments, Form D of Compound A may be characterized by thermal analysis. A representative DSC plot for Form D of Compound A is shown in FIG. 11. In certain embodiments, Form D is characterized by a DSC plot comprising an endothermic event with an onset temperature of about 283° C. In certain embodiments, a characteristic Form D DSC plot further comprises one additional event, such as, e.g., an endothermic event with a peak temperature of about 114° C. A representative TGA plot for Form D of Compound A is shown in FIG. 12. In certain embodiments, Form D is characterized by a TGA plot comprising a mass loss of less than about 10%, less than about 8%, less than about 6%, less than about 4%, e.g., about 3%, of the total mass of the sample upon heating from about 25° C. to about 150° C. In certain embodiments, the TGA mass loss event comprises the loss of water. In certain embodiments, Form D of Compound A is solvated. In certain embodiments, Form D is hydrated.

In certain embodiments, Form D of Compound A may be characterized by moisture sorption analysis. In certain embodiments, when the RH is increased from about 0% to about 95% RH, Form D exhibits a mass change of less than about 5%, e.g., about 4%, of the starting mass of the sample. In certain embodiments, mass gained upon adsorption is lost when the RH is decreased back to about 0% RH.

Certain embodiments herein provide Form D of Compound A which is substantially pure. Certain embodiments herein provide Form D of Compound A which is substantially free of other solid forms comprising Compound A including, e.g., Forms A, B, C, D, E, F, and/or an amorphous solid form comprising Compound A as provided herein, and Form A1 and an amorphous solid form comprising Compound A hydrochloride as provided herein. Certain embodiments herein provide Form D as a mixture of solid forms comprising Compound A, including, e.g., a mixture comprising one or more of the following: Forms A, B, C, E, F, and an amorphous solid form comprising Compound A as provided herein, and Form A1 and an amorphous solid form comprising Compound A hydrochloride as provided herein.

4.1.5. Form E of Compound A

Certain embodiments herein provide the Form E crystal form of Compound A. In certain embodiments, Form E of Compound A can be obtained from various solvents, including, but not limited to, solvent systems comprising acetonitrile or isopropanol, and mixtures thereof. In certain embodiments, Form E can be obtained using a slurry recrystallization process. In certain embodiments, Form E can be obtained using a slurry recrystallization process at room temperature. Form E can also be obtained by an antisolvent recrystallization process by dissolving Compound A in DMF or NMP and rapidly adding water as antisolvent.

In certain embodiments, Form E of Compound A may be characterized by X-ray powder diffraction analysis. A representative XRPD pattern of Form E of Compound A is provided in FIG. 13. In certain embodiments, Form E of Compound A is characterized by XRPD peaks located at one, two, three, four, five, six, seven, eight, nine, ten, eleven, twelve or thirteen of the following approximate positions: 7.3, 9.3, 12.2, 14.0, 14.6, 15.7, 16.8, 21.0, 22.0, 22.7, 29.4, 30.0 and 37.0 degrees 2θ. In one embodiment, Form E of Compound A is characterized by XRPD peaks located at the following approximate positions: 7.3, 14.6, 22.0, 30.0 and 37.0 degrees 2θ. In certain embodiments, Form E of Compound A is characterized by an XRPD pattern which matches the pattern exhibited in FIG. 13. In certain embodiments, Form E of Compound A is characterized by an XRPD pattern having 1, 2, 3, 4, 5, 6, 7, 8, 9, 10, 11, 12 or 13 peaks matching peaks in the representative Form E pattern provided herein.

Figure 14:
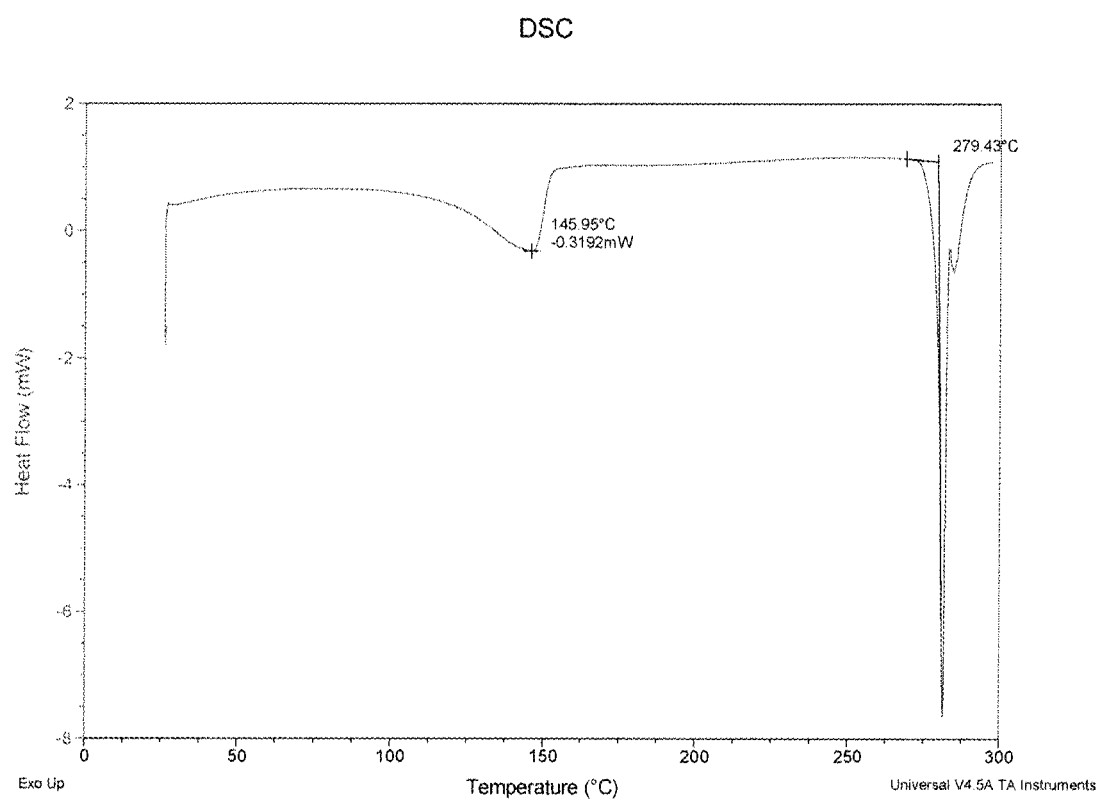
Figure 15:
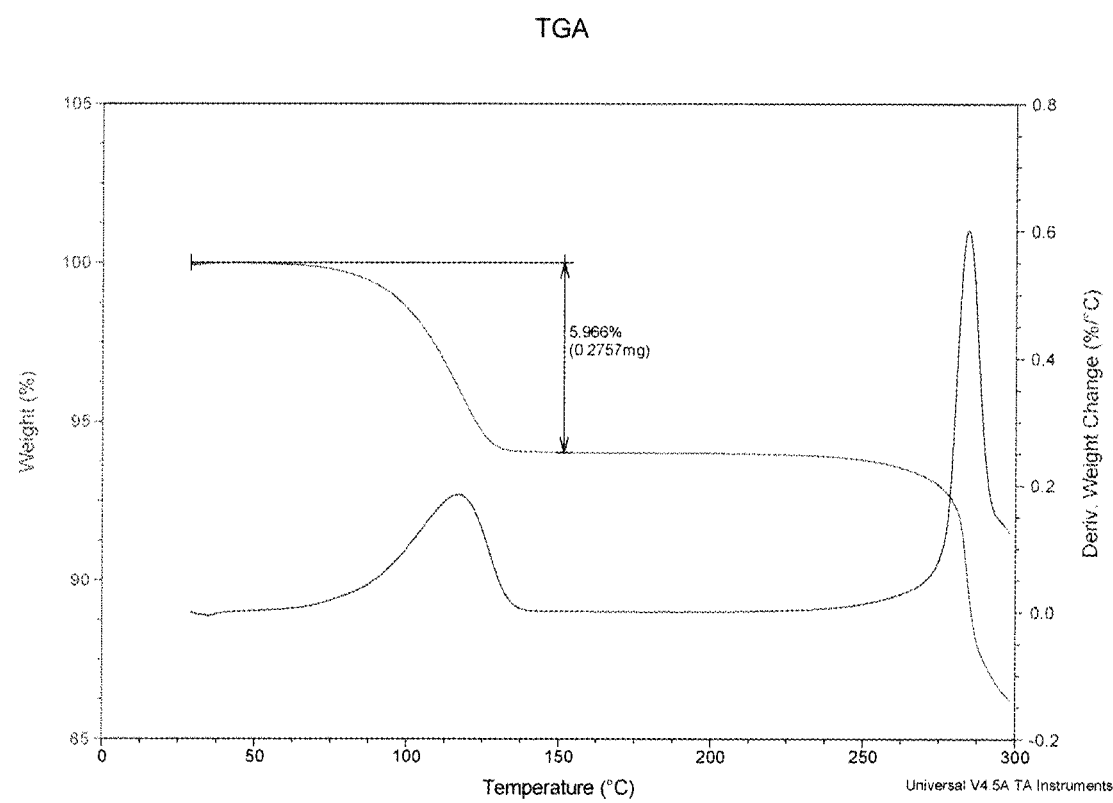

In certain embodiments, Form E of Compound A may be characterized by thermal analysis. A representative DSC plot for Form E of Compound A is shown in FIG. 14. In certain embodiments, Form E is characterized by a DSC plot comprising an endothermic event with an onset temperature of about 279° C. In certain embodiments, a characteristic Form E DSC plot further comprises one additional event, such as, e.g., an endothermic event with a peak temperature of about 146° C. A representative TGA plot for Form E of Compound A is shown in FIG. 15. In certain embodiments, Form E is characterized by a TGA plot comprising a mass loss of less than about 10%, less than about 8%, less than about 6%, e.g., about 5.97%, of the total mass of the sample upon heating from about 25° C. to about 150° C. In certain embodiments, the TGA mass loss event comprises the loss of water. In certain embodiments, Form E of Compound A is solvated. In certain embodiments, Form E is hydrated.

In certain embodiments, Form E of Compound A may be characterized by moisture sorption analysis. In certain embodiments, when the RH is increased from about 0% to about 95% RH, Form E exhibits a mass change of less than about 2%, less than about 1%, or less than about 0.5%, e.g., about 0.4%, of the starting mass of the sample. In certain embodiments, mass gained upon adsorption is lost when the RH is decreased back to about 0% RH. In certain embodiments, Form E is nonhygroscopic. In certain embodiments, the XRPD pattern of Form E material is substantially unchanged following the adsorption/desorption analysis. In certain embodiments, Form E is stable with respect to humidity.

Certain embodiments herein provide Form E of Compound A which is substantially pure. Certain embodiments herein provide Form E of Compound A which is substantially free of other solid forms comprising Compound A including, e.g., Forms A, B, C, D, F, and/or an amorphous solid form comprising Compound A as provided herein, and Form A1 and an amorphous solid form comprising Compound A hydrochloride as provided herein. Certain embodiments herein provide Form E as a mixture of solid forms comprising Compound A, including, e.g., a mixture comprising one or more of the following: Forms A, B, C, D, F, and an amorphous solid form comprising Compound A as provided herein, and Form A1 and an amorphous solid form comprising Compound A hydrochloride as provided herein.

4.1.6. Form F of Compound A

Certain embodiments herein provide the Form F crystal form of Compound A. In certain embodiments, Form F of Compound A can be obtained from various solvents, including, but not limited to, solvent systems comprising water. In certain embodiments, Form F can be obtained using a slurry recrystallization process.

In certain embodiments, Form F of Compound A may be characterized by X-ray powder diffraction analysis. A representative XRPD pattern of Form F of Compound A is provided in FIG. 16. In certain embodiments, Form F of Compound A is characterized by XRPD peaks located at one, two, three, four, five, six, seven, eight, nine or ten of the following approximate positions: 7.2, 9.1, 14.5, 15.7, 16.8, 18.3, 21.9, 22.7, 29.9 and 36.9 degrees 2θ. In one embodiment, Form F of Compound A is characterized by XRPD peaks located at the following approximate positions: 14.5, 15.7, 22.7 and 29.9 degrees 2θ. In certain embodiments, Form F of Compound A is characterized by an XRPD pattern which matches the pattern exhibited in FIG. 16. In certain embodiments, Form F of Compound A is characterized by an XRPD pattern having 1, 2, 3, 4, 5, 6, 7, 8, 9 or 10 peaks matching peaks in the representative Form F pattern provided herein.

Figure 17:
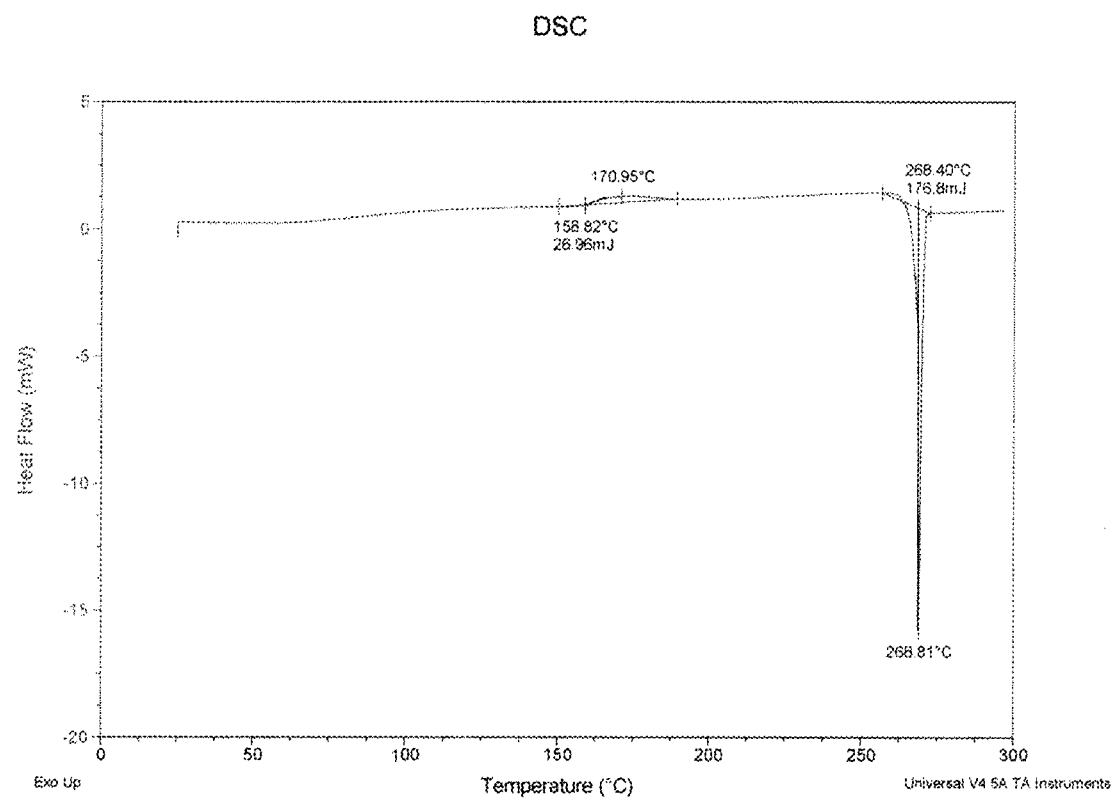

In certain embodiments, Form F of Compound A may be characterized by thermal analysis. A representative DSC plot for Form F of Compound A is shown in FIG. 17. In certain embodiments, Form F is characterized by a DSC plot comprising an endothermic event with an onset temperature of about 267° C. In certain embodiments, a characteristic Form F DSC plot further comprises one additional event, such as, e.g., an exothermic event with a peak temperature of about 170° C. In certain embodiments, Form F is solvated. In certain embodiments, Form F is hydrated.

Certain embodiments herein provide Form F of Compound A which is substantially pure. Certain embodiments herein provide Form F of Compound A which is substantially free of other solid forms comprising Compound A including, e.g., Forms A, B, C, D, E, and/or an amorphous solid form comprising Compound A as provided herein, and Form A1 and an amorphous solid form comprising Compound A hydrochloride as provided herein. Certain embodiments herein provide Form F as a mixture of solid forms comprising Compound A, including, e.g., a mixture comprising one or more of the following: Forms A, B, C, D, E, and an amorphous solid form comprising Compound A as provided herein, and Form A1 and an amorphous solid form comprising Compound A hydrochloride as provided herein.

4.1.7. Form A1 of Compound A Hydrochloride

Certain embodiments herein provide crystalline Form A1 of a hydrochloride salt of Compound A. In certain embodiments, Form A1 can be obtained from various solvents, including, but not limited to, solvent systems comprising acetone, acetonitrile, n-butanol, ethanol, ethyl acetate, heptane, methanol, methylene chloride, methyl ethyl ketone, methyl t-butyl ether, 2-propanol, toluene, tetrahydrofuran, water, and mixtures thereof. In certain embodiments, Form A1 can be obtained using a fast or slow cooling crystallization process. In certain embodiments, Form A1 can be obtained using an antisolvent addition crystallization process.

Form A1 of Compound A hydrochloride is a stable crystalline form. For example, Form A1 found to be chemically stable upon storage at room temperature, exposed to air and light, for 6 weeks. Form A1 was also found to be chemically stable upon storage at 40° C. under vacuum. Form A1 was also found to be chemically stable upon storage at 40° C. under a nitrogen atmosphere. Form A1 was also found to be chemically stable upon storage at 40° C. and 75% relative humidity (RH). Form A1 was also found to be chemically stable upon storage at 60° C. in a closed container. Based on this data, Form A1 of Compound A was determined to be suitably stable for large scale production (Example 5.4.3.2).

In certain embodiments, Form A1 may be characterized by X-ray powder diffraction analysis. A representative XRPD pattern of Form A1 is provided in FIG. 18. In certain embodiments, Form A1 is characterized by XRPD peaks located at one, two, three, four, five, six, seven, eight, nine or ten of the following approximate positions: 8.6, 11.3, 13.1, 15.3, 17.3, 20.5, 22.7, 23.6, 26.3 and 31.4 degrees 2θ. In one embodiment, Form A1 is characterized by XRPD peaks located at the following approximate positions: 8.6, 13.1, 20.5 and 26.3 degrees 2θ. In certain embodiments, Form A1 is characterized by an XRPD pattern which matches the pattern exhibited in FIG. 18. In certain embodiments, Form A1 is characterized by an XRPD pattern having 1, 2, 3, 4, 5, 6, 7, 8, 9 or 10 peaks matching peaks in the representative Form A1 pattern provided herein.

Figure 19:
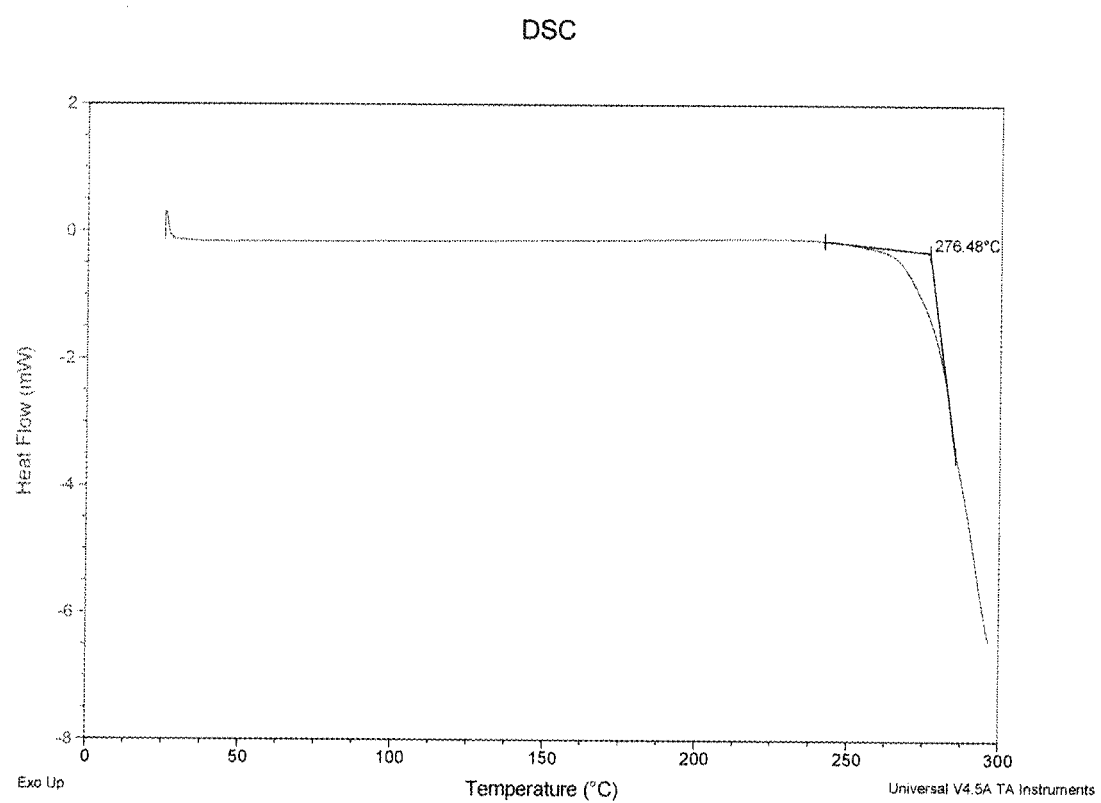
Figure 20:
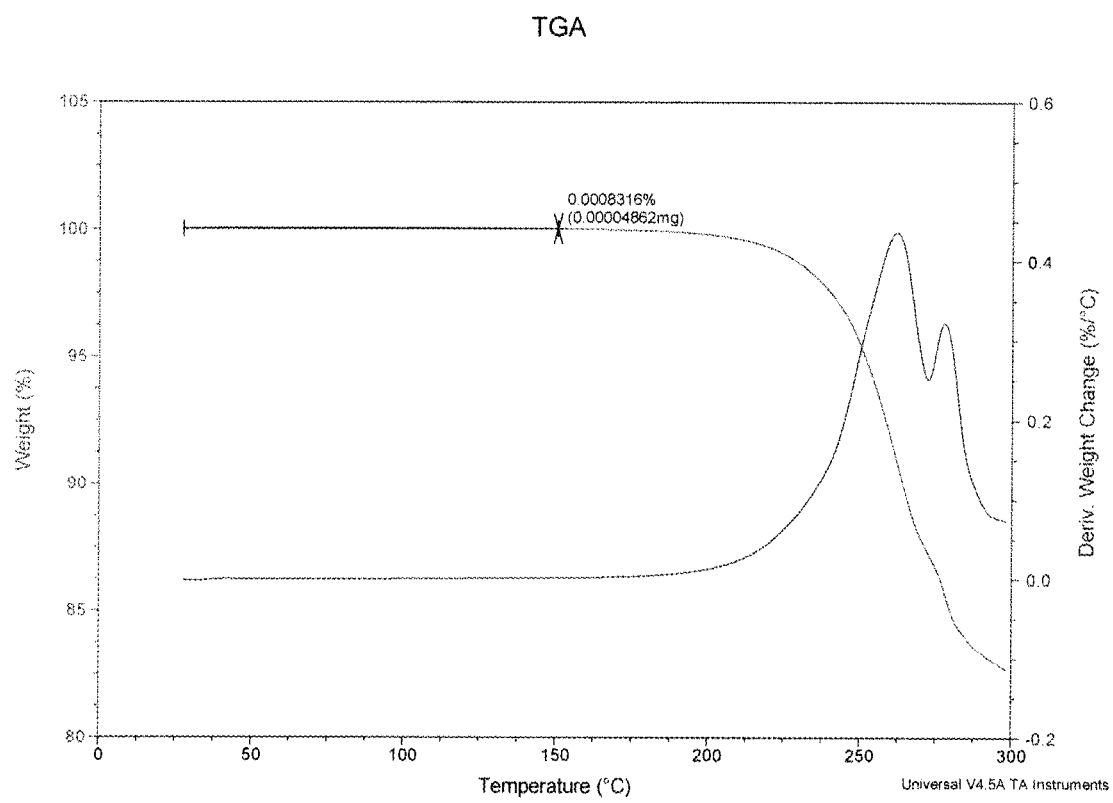

In certain embodiments, Form A1 of a hydrochloride salt of Compound A may be characterized by thermal analysis. A representative DSC plot for Form A1 is shown in FIG. 19. In certain embodiments, Form A1 is characterized by a DSC plot comprising an endothermic event with an onset temperature of about 276° C. In certain embodiments, Form A1 has a decomposition temperature at about 276° C. A representative TGA plot for Form A1 of Compound A is shown in FIG. 20. In certain embodiments, Form A1 is characterized by a TGA plot comprising a mass loss of less than about 1%, less than about 0.5%, less than about 0.2%, less than about 0.1%, less than about 0.05%, less than about 0.01%, e.g., about 0.0008%, of the total mass of the sample upon heating from about 25° C. to about 150° C. In certain embodiments, Form A1 of Compound A does not contain substantial amounts of either water or other solvent in the crystal lattice. In certain embodiments, Form A1 is unsolvated. In certain embodiments, Form A1 is anhydrous.

Figure 21:
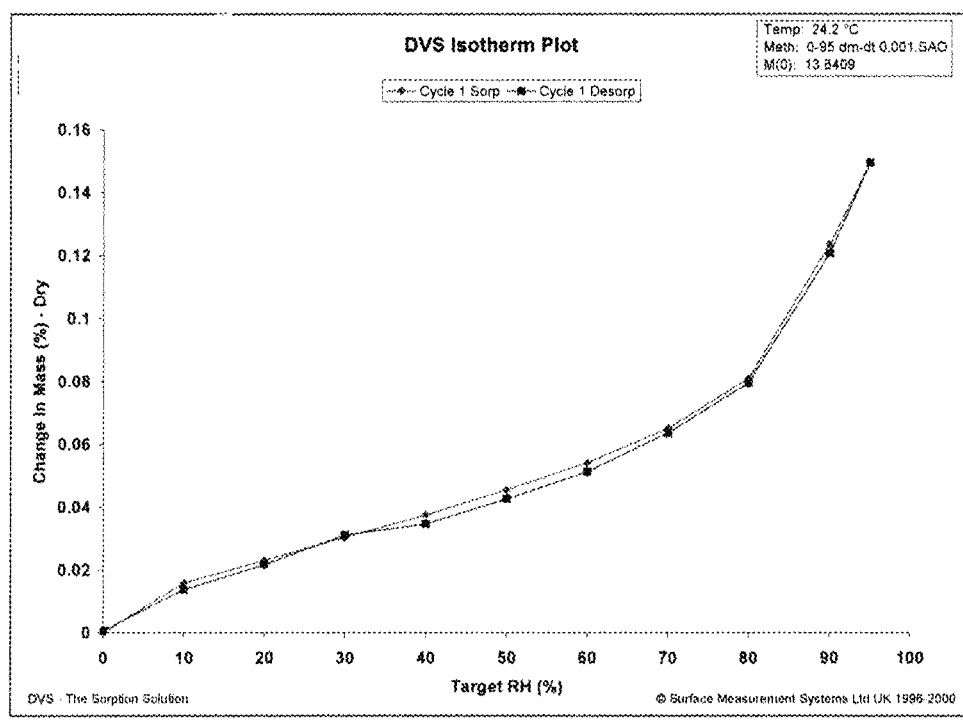
Figure 22:
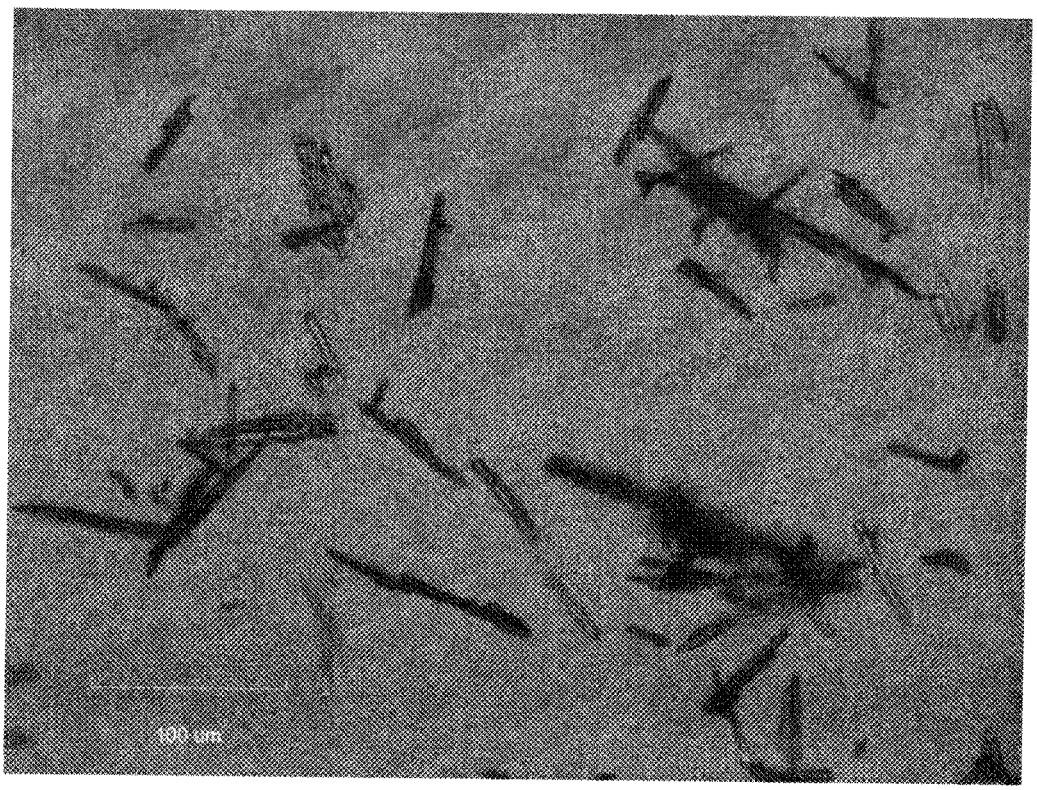
FIG. 22 is a microscopic image of crystals of Form A1 of 3-(5-amino-2-methyl-4-oxo-4H-quinazolin-3-yl)-piperidine-2,6-dione hydrochloride.

In certain embodiments, Form A1 may be characterized by moisture sorption analysis. A representative moisture sorption isotherm plot is shown in FIG. 21. In certain embodiments, when the relative humidity ("RH") is increased from about 0% to about 95% RH, Form A1 exhibits a mass change of less than about 1%, less than about 0.5%, less than about 0.2% (e.g., about 0.15%) of the starting mass of the sample. In certain embodiments, mass gained upon adsorption is lost when the RH is decreased back to about 0% RH. Accordingly, in certain embodiments, Form A1 is substantially nonhygroscopic. In certain embodiments, the XRPD pattern of the Form A1 material is substantially unchanged following the adsorption/desorption analysis. In certain embodiments, Form A1 is stable with respect to humidity.

In certain embodiments, Form A1 of a hydrochloride salt of Compound A may be characterized by its stability profile. In certain embodiments, Form A1 material is stable, e.g., its XRPD pattern remains substantially unchanged, upon exposure to elevated temperature, upon exposure to elevated humidity, upon exposure to one or more solvents, and/or upon compression. In certain embodiments, for example, Form A1 is stable following exposure to an environment of about 40° C. and about 75% RH environment for about four weeks. In certain embodiments, for example, Form A1 is stable following exposure to an environment of room temperature and about 95% RH environment for about four days. In certain embodiments, Form A1 is stable following exposure to one or more solvent systems comprising, e.g., acetone, acetonitrile, n-butanol, ethanol, ethyl acetate, heptane, methanol, methylene chloride, methyl ethyl ketone, methyl t-butyl ether, 2-propanol, toluene, and/or tetrahydrofuran at about 50° C. for at least about 24 hrs. In certain embodiments, Form A1 is stable upon compression at about 2,000-psi pressure for about one minute.

In certain embodiments, Form A1 may be characterized by particle analysis. In certain embodiments, a sample of Form A1 comprises particles having an acicular morphology.

Certain embodiments herein provide Form A1 Compound A which is substantially pure. Certain embodiments herein provide Form A1 of a hydrochloride salt of Compound A, which is substantially free of other solid forms comprising Compound A, including, e.g., an amorphous solid form comprising a hydrochloride salt of Compound A as provided herein, and Forms A, B, C, D, E, F, and/or an amorphous solid form comprising Compound A as provided herein. Certain embodiments herein provide Form A1 as a mixture of solid forms comprising Compound A, including, e.g., a mixture comprising one or more of the following: Forms A, B, C, D, E, F, and an amorphous solid form comprising Compound A as provided herein, and an amorphous solid form comprising Compound A hydrochloride as provided herein.

Certain embodiments herein provide Form A1 of a hydrochloride salt of Compound A, wherein the molar ratio of Compound A and hydrochloride in Form A1 is ranging from about 0.1 to about 10, from about 0.2 to about 5, from about 0.5 to about 2, from about 0.6 to about 1.5, from about 0.7 to about 1.3, from about 0.8 to about 1.2, from about 0.9 to about 1.1, or from about 0.95 to about 1.05. In certain embodiments, the molar ratio of Compound A and hydrochloride in Form A1 is about 0.5, about 0.6, about 0.7, about 0.8, about 0.9, about 0.95, about 1, about 1.05, about 1.1, about 1.2, about 1.3, about 1.4, or about 1.5.

4.2. Methods of Treatment

The disclosure encompasses methods of treating, preventing, and/or managing various diseases or disorders using a solid form of Compound A or a stereoisomer thereof, or a pharmaceutically acceptable salt, solvate, hydrate, co-crystal, clathrate, or polymorph thereof, which comprise administering a therapeutically or prophylactically effective amount of one or more solid forms comprising Compound A, such as, e.g., Form A, B, C, D, E, or an amorphous form of Compound A, or Form A1 or an amorphous form of Compound A hydrochloride as provided herein.

Without being limited by a particular theory, Compound A can control angiogenesis or inhibit the production of certain cytokines including, but not limited to, TNF-α, IL-1β, IL-12, IL-18, GM-CSF, and/or IL-6. Without being limited by a particular theory, Compound A can stimulate the production of certain other cytokines including IL-10, and also act as a costimulatory signal for T cell activation, resulting in increased production of cytokines such as, but not limited to, IL-12 and/or IFN-γ. In addition, Compound A can enhance the effects of NK cells and antibody-mediated cellular cytotoxicity (ADCC). Further, Compound A may be immunomodulatory and/or cytotoxic, and thus, may be useful as chemotherapeutic agents. Consequently, without being limited by a particular theory, some or all of such characteristics possessed by Compound A may render them useful in treating, managing, and/or preventing various diseases or disorders.

Examples of diseases or disorders include, but are not limited to, cancer, disorders associated with angiogenesis, pain including, but not limited to, Complex Regional Pain Syndrome ("CRPS"), Macular Degeneration ("MD") and related syndromes, skin diseases, pulmonary disorders, asbestos-related disorders, parasitic diseases, immunodeficiency disorders, CNS disorders, CNS injury, atherosclerosis and related disorders, dysfunctional sleep and related disorders, hemoglobinopathy and related disorders (e.g., anemia), TNFα related disorders, and other various diseases and disorders.

Examples of cancer and precancerous conditions include, but are not limited to, those described in U.S. Pat. Nos. 6,281,230 and 5,635,517 to Muller et al., in various U.S. patent publications to Zeldis, including publication nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in WO 2004/103274, published Dec. 2, 2004. All of these references are incorporated herein in their entireties by reference.

Specific examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are also useful for treating cancers of the blood and bone marrow, such as multiple myeloma and acute and chronic leukemias, for example, lymphoblastic, myelogenous, lymphocytic, and myelocytic leukemias. The compounds provided herein can be used for treating, preventing or managing either primary or metastatic tumors.

Other specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

In one embodiment, provided herein are methods of treating, preventing or managing various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. publication no. 2006/0030594, published Feb. 9, 2006, which is incorporated in its entirety by reference.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another embodiment, provided herein are methods of treating, preventing or managing various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma (MCL), lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), follicular lymphoma, and any type of the mantle cell lymphomas that can be seen under the microscope (nodular, diffuse, blastic and mentle zone lymphoma).

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the diseases and disorders associated with, or characterized by, undesired angiogenesis include, but are not limited to, arthritis, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

Examples of pain include, but are not limited to those described in U.S. patent publication no. 2005/0203142, published Sep. 15, 2005, which is incorporated herein by reference. Specific types of pain include, but are not limited to, nociceptive pain, neuropathic pain, mixed pain of nociceptive and neuropathic pain, visceral pain, migraine, headache and post-operative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine and velcade.

As used herein, the terms "complex regional pain syndrome," "CRPS" and "CRPS and related syndromes" mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Examples of MD and related syndromes include, but are not limited to, those described in U.S. patent publication no. 2004/0091455, published May 13, 2004, which is incorporated herein by reference. Specific examples include, but are not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

Examples of skin diseases include, but are not limited to, those described in U.S. publication no. 2005/0214328A1, published Sep. 29, 2005, which is incorporated herein by reference. Specific examples include, but are not limited to, keratoses and related symptoms, skin diseases or disorders characterized with overgrowths of the epidermis, acne, and wrinkles.

As used herein, the term "keratosis" refers to any lesion on the epidermis marked by the presence of circumscribed overgrowths of the horny layer, including but not limited to actinic keratosis, seborrheic keratosis, keratoacanthoma, keratosis follicularis (Darier disease), inverted follicular keratosis, palmoplantar keratoderma (PPK, keratosis palmaris et plantaris), keratosis pilaris, and stucco keratosis. The term "actinic keratosis" also refers to senile keratosis, keratosis senilis, verruca senilis, plana senilis, solar keratosis, keratoderma or keratoma. The term "seborrheic keratosis" also refers to seborrheic wart, senile wart, or basal cell papilloma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratoses, papillomatosis, hyperpigmentation of the basal cells, cellular atypia, mitotic figures, abnormal cell-cell adhesion, dense inflammatory infiltrates and small prevalence of squamous cell carcinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratoses, sign of Leser-Trélat, warty dyskeratoma (WD), trichostasis spinulosa (TS), erythrokeratodermia variabilis (EKV), ichthyosis fetalis (harlequin ichthyosis), knuckle pads, cutaneous melanoacanthoma, porokeratosis, psoriasis, squamous cell carcinoma, confluent and reticulated papillomatosis (CRP), acrochordons, cutaneous horn, cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Examples of pulmonary disorders include, but are not limited to, those described in U.S. publication no. 2005/0239842A1, published Oct. 27, 2005, which is incorporated herein by reference. Specific examples include pulmonary hypertension and related disorders. Examples of pulmonary hypertension and related disorders include, but are not limited to: primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vasular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

Examples of asbestos-related disorders include, but not limited to, those described in U.S. publication no. 2005/0100529, published May 12, 2005, which is incorporated herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. publication no. 2006/0154880, published Jul. 13, 2006, which is incorporated herein by reference. Parasitic diseases include diseases and disorders caused by human intracellular parasites such as, but not limited to, *P. falcifarium, P. ovale, P. vivax, P. malariae, L. donovari, L. infantum, L. aethiopica, L. major, L. tropica, L. mexicana, L. braziliensis, T. Gondii, B. microti, B. divergens, B. coli, C. parvum, C. cayetanensis, E. histolytica, I. belli, S. mansonii, S. haematobium, Trypanosoma* ssp., *Toxoplasma* ssp., and *O. volvulus*. Other diseases and disorders caused by non-human intracellular parasites such as, but not limited to, *Babesia bovis, Babesia canis, Banesia Gibsoni, Besnoitia darlingi, Cytauxzoon felis, Eimeria* ssp., *Hammondia* ssp., and *Theileria* ssp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis, and dermatitis caused by animal schistosomes.

Examples of immunodeficiency disorders include, but are not limited to, those described in U.S. application Ser. No. 11/289,723, filed Nov. 30, 2005. Specific examples include, but not limited to, adenosine deaminase deficiency, antibody deficiency with normal or elevated Igs, ataxia-tenlangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

Examples of CNS disorders include, but are not limited to, those described in U.S. publication no. 2005/0143344, published Jun. 30, 2005, which is incorporated herein by reference. Specific examples include, but are not limited to, include, but are not limited to, Amyotrophic Lateral Sclerosis, Alzheimer Disease, Parkinson Disease, Huntington's Disease, Multiple Sclerosis other neuroimmunological disorders such as Tourette Syndrome, delerium, or disturbances in consciousness that occur over a short period of time, and amnestic disorder, or discreet memory impairments that occur in the absence of other central nervous system impairments.

Examples of CNS injuries and related syndromes include, but are not limited to, those described in U.S. publication no. 2006/0122228, published Jun. 8, 2006, which is incorporated herein by reference. Specific examples include, but are not limited to, CNS injury/damage and related syndromes, include, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Other disease or disorders include, but not limited to, viral, genetic, allergic, and autoimmune diseases. Specific examples include, but not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory-bowel disease, multiple sclerosis, systemic lupus erythrematosus, ENL in leprosy, radiation damage, cancer, asthma, or hyperoxic alveolar injury.

Examples of atherosclerosis and related conditions include, but are not limited to, those disclosed in U.S. publication no. 2002/0054899, published May 9, 2002, which is incorporated herein by reference. Specific examples include, but are not limited to, all forms of conditions involving atherosclerosis, including restenosis after vascular intervention such as angioplasty, stenting, atherectomy and grafting. All forms of vascular intervention are contemplated herein, including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary by-pass grafting, angioplasty with stent implantation, peripheral percutaneous transluminal intervention of the iliac, femoral or popliteal arteries, and surgical intervention using impregnated artificial grafts.

Examples of dysfunctional sleep and related syndromes include, but are not limited to, those disclosed in U.S. publication no. 2005/0222209A1, published Oct. 6, 2005, which is incorporated herein by reference. Specific examples include, but are not limited to, snoring, sleep apnea, insomnia, narcolepsy, restless leg syndrome, sleep terrors, sleep walking sleep eating, and dysfunctional sleep associated with chronic neurological or inflammatory conditions. Chronic neurological or inflammatory conditions, include, but are not limited to, Complex Regional Pain Syndrome, chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, post-herpetic, traumatic or inflammatory), and neurodegenerative disorders such as Parkinson's Disease, Alzheimer's Disease, amyotrophic lateral sclerosis, multiple sclerosis, Huntington's Disease, bradykinesia; muscle rigidity; parkinsonian tremor; parkinsonian gait; motion freezing; depression; defective long-term memory, Rubinstein-Taybi syndrome (RTS); dementia; postural instability; hypokinetic disorders; synuclein disorders; multiple system atrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease with parkinsonism; Wilson disease; Hallervorden-Spatz disease; Chediak-Hagashi disease; SCA-3 spinocerebellar ataxia; X-linked dystonia parkinsonism; prion disease; hyperkinetic disorders; chorea; ballismus; dystonia tremors; Amyotrophic Lateral Sclerosis (ALS); CNS trauma and myoclonus.

Examples of hemoglobinopathy and related disorders include, but are not limited to, those described in U.S. publication no. 2005/0143420A1, published Jun. 30, 2005, which is incorporated herein by reference. Specific examples include, but are not limited to, hemoglobinopathy, sickle cell anemia, and any other disorders related to the differentiation of CD34+ cells.

Examples of TNFα related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; Graft versus Host Reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; other disorders such as rheumatoid arthritis, rheumatoid spondylitis, osteoarthritis, psoriatic arthritis and other arthritic conditions, septic shock, septis, endotoxic shock, graft versus host disease, wasting, Crohn's disease, ulcerative colitis, multiple sclerosis, systemic lupus erythromatosis, ENL in leprosy, HIV, AIDS, and opportunistic infections in AIDS; disorders such as septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

In other embodiments, the use of Compound A in various immunological applications, in particular, as vaccine adjuvants, particularly anticancer vaccine adjuvants, as disclosed in U.S. Provisional Application No. 60/712,823, filed Sep. 1, 2005, which is incorporated herein in its entirety by reference, is also encompassed. These embodiments also relate to the use of Compound A in combination with vaccines to treat or prevent cancer or infectious diseases, and other various uses of immunomodulatory compounds such as reduction or desensitization of allergic reactions.

Doses of a solid form of Compound A vary depending on factors such as: specific indication to be treated, prevented, or managed; age and condition of a patient; and amount of second active agent used, if any. Generally, a solid form of Compound A provided herein may be used in an amount of from about 0.1 mg to about 500 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

A solid form of Compound A provided herein can be combined with other pharmacologically active compounds ("second active agents") in methods and compositions provided herein. Certain combinations may work synergistically in the treatment of particular types of diseases or disorders, and conditions and symptoms associated with such diseases or disorders. A solid form of Compound A provided herein can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylyase inhibitors (such as, for example, SAHA and LAQ824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, anticancer agents and antibiotics (e.g., clarithromycin).

Specific second active compounds that can be combined with a solid form of Compound A provided herein vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA;

arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in mutiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In another embodiment, examples of specific second agents according to the indications to be treated, prevented, or managed can be found in the following references, all of which are incorporated herein in their entireties: U.S. Pat. Nos. 6,281,230 and 5,635,517; U.S. publication nos. 2004/0220144, 2004/0190609, 2004/0087546, 2005/0203142, 2004/0091455, 2005/0100529, 2005/0214328, 2005/0239842, 2006/0154880, 2006/0122228, and 2005/0143344; and U.S. provisional application No. 60/631,870.

Examples of second active agents that may be used for the treatment, prevention and/or management of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate (Aspirin®), celecoxib (Celebrex®), Enbrel®, ketamine, gabapentin (Neurontin®), phenyloin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac), sertraline (Zoloft®), naproxen, nefazodone (Serzone®), venlafaxine (Effexor®), trazodone (Desyrel®), bupropion (Wellbutrin®), mexiletine, nifedipine, propranolol, tramadol, lamotrigine, vioxx, ziconotide, ketamine, dextromethorphan, benzodiazepines, baclofen, tizanidine and phenoxybenzamine.

Examples of second active agents that may be used for the treatment, prevention and/or management of macular degeneration and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2α, pentoxifylline, tin etiopurpurin, motexafin, lucentis, lutetium, 9-fluoro-11,21-dihydroxy-16,17-1-methylethylidinebis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O—Ac genistin, daidzein, daidzin, 6'-O-Mal daidzin, 6'-O—Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited herein are incorporated in their entireties by reference.

Examples of second active agents that may be used for the treatment, prevention and/or management of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of second active agents that may be used for the treatment, prevention and/or management of pulmonary hepertension and related disorders include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin I2 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Clalis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of second active agents that may be used for the treatment, prevention and/or management of asbestos-related disorders include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of second active agents that may be used for the treatment, prevention and/or management of parasitic diseases include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stibogluconate), interfereon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment, prevention and/or management of immunodeficiency disorders include, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment, prevention and/or management of CNS disorders include, but are not limited to: opioids; a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises 1-threo-methylphenidate, d-threo-methylphenidate, dl-threo-methylphenidate, 1-erythro-methylphenidate, d-erythro-methylphenidate, dl-erythro-methylphenidate, and a mixture thereof; and a diuretic agent such as, but not limited to, mannitol, furosemide, glycerol, and urea.

Examples of second active agent that may be used for the treatment, prevention and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of hemoglobinopathy and related disorders include, but are not limited to:

interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; hydroxy urea; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

Administration of a solid form of Compound A provided herein and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One of administration for a solid form of Compound A provided herein is oral. Routes of administration for the second active agents or ingredients are known to those of ordinary skill in the art. See, e.g., *Physicians' Desk Reference* (60$^{th}$ ed., 2006).

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

In certain embodiments, the prophylactic or therapeutic agents provided herein are cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in one embodiment, a solid form of Compound A provided herein is administered daily in a single or divided doses in a four to six week cycle with a rest period of about a week or two weeks. Cycling therapy further allows the frequency, number, and length of dosing cycles to be increased. Thus, another embodiment encompasses the administration of a compound provided herein for more cycles than are typical when it is administered alone. In yet another embodiment, a compound provided herein is administered for a greater number of cycles than would typically cause dose-limiting toxicity in a patient to whom a second active ingredient is not also being administered.

In one embodiment, a solid form of Compound A provided herein is administered daily and continuously for three or four weeks at a dose of from about 0.1 mg to about 500 mg per day, followed by a rest of one or two weeks. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In one embodiment, a solid form of Compound A provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

4.3. Pharmaceutical Compositions

Pharmaceutical compositions and single unit dosage forms comprising one or more solid forms comprising Compound A are provided herein. Also provided herein are methods for preparing pharmaceutical compositions and single unit dosage forms comprising one or more solid forms comprising Compound A. For example, in certain embodiments, individual dosage forms comprising a solid form provided herein or prepared using solid form provided herein may be suitable for oral, mucosal (including rectal, nasal, or vaginal), parenteral (including subcutaneous, intramuscular, bolus injection, intraarterial, or intravenous), sublingual, transdermal, buccal, or topical administration.

In certain embodiments, pharmaceutical compositions and dosage forms provided herein comprise one or more solid forms comprising Compound A. Certain embodiments herein provide pharmaceutical compositions and dosage forms comprising a solid form comprising Compound A, such as, e.g., Forms A, B, C, D, E, F or an amorphous solid form comprising Compound A as provided herein, or Form A1 or an amorphous solid form comprising Compound A hydrochloride as provided herein, wherein the solid form comprising Compound A substantially pure. Certain embodiments herein provide pharmaceutical compositions and dosage forms comprising a solid form comprising Compound A, such as, e.g., Forms A, B, C, D, E, F, or an amorphous solid form comprising Compound A as provided herein, or Form A1 or an amorphous solid form comprising Compound A hydrochloride as provided herein, which is substantially free of other solid forms comprising Compound A including, e.g., Forms A, B, C, D, E, F, and/or an amorphous solid form comprising Compound A as provided herein, and Form A1 and/or an amorphous solid form comprising Compound A hydrochloride as provided herein. Certain embodiments herein provide pharmaceutical compositions and dosage forms comprising a mixture of solid forms comprising Compound A, including, e.g., a mixture comprising one or more of the following: Forms A, B, C, D, E, F, and an amorphous solid form comprising Compound A as provided herein, and Form A1 and an amorphous solid form comprising Compound A hydrochloride as provided herein. Pharmaceutical compositions and dosage forms provided herein typically also comprise one or more pharmaceutically acceptable excipient, diluent or carrier.

A particular pharmaceutical composition encompassed by this embodiment comprises one or more solid forms comprising Compound A and at least one additional therapeutic agent. Examples of additional therapeutic agents include, but are not limited to: anti-cancer drugs and anti-inflammation therapies including, but not limited to, those provided herein.

Single unit dosage forms of the disclosure are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the disclosure will typically vary depending on their use. For example, a dosage form used in the acute treatment of inflammation or a related disorder may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

Lactose-free compositions of the disclosure can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This disclosure further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The disclosure further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms provided herein lie within the range of from about 1 mg to about 1,000 mg per day, given as a single once-a-day dose in the morning but preferably as divided doses throughout the day. More specifically, the daily dose is administered twice daily in equally divided doses. Specifically, a daily dose range may be from about 5 mg to about 500 mg per day, more specifically, between about 10 mg and about 200 mg per day. In managing the patient, the therapy may be initiated at a lower dose, perhaps about 1 mg to about 25 mg, and increased if necessary up to about 200 mg to about 1,000 mg per day as either a single dose or divided doses, depending on the patient's global response.

4.3.1. Oral Dosage Forms

Pharmaceutical compositions of the disclosure that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally Remington's Pharmaceutical Sciences, 18th ed., Mack Publishing, Easton Pa. (1990).

Typical oral dosage forms of the disclosure are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Suitable forms of microcrystalline cellulose include, but are not limited to, the materials sold as AVICEL-PH-101™, AVICEL-PH-103™, AVICEL RC-581™, AVICEL-PH-105™ (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581™. Suitable anhydrous or low moisture excipients or additives include AVICEL-PH-103™ and Starch 1500 LM™.

Disintegrants are used in the compositions of the disclosure to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the disclosure. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200™, manufactured by W.R. Grace Co. of Baltimore, Md.), a coagulated aerosol of synthetic silica (marketed by Degussa Co. of Plano, Tex.), CAB-O-SIL™ (a pyrogenic silicon dioxide product sold by Cabot Co. of Boston, Mass.), and mixtures thereof. If used at all, lubricants are typically used in an amount of less than about one weight percent of the pharmaceutical compositions or dosage forms into which they are incorporated.

4.3.2. Delayed Release Dosage Forms

Solid forms comprising Compound A as provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.3.3. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the disclosure are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the disclosure.

4.3.4. Transdermal, Topical, and Mucosal Dosage Forms

Transdermal, topical, and mucosal dosage forms of the disclosure include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this disclosure are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the disclosure. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80™ (polysorbate 80) and Span 60™ (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different solid forms comprising the active ingredients can be used to further adjust the properties of the resulting composition.

4.3.5. Kits

This disclosure encompasses kits which, when used by the medical practitioner, can simplify the administration of appropriate amounts of active ingredients to a patient.

A typical kit of the disclosure comprises a unit dosage form of compound A, or a pharmaceutically acceptable solid form or prodrug thereof, and a unit dosage form of a second active ingredient. Examples of second active ingredients include, but are not limited to, those listed herein.

Kits of the disclosure can further comprise devices that are used to administer the active ingredient(s). Examples of such devices include, but are not limited to, syringes, drip bags, patches, and inhalers.

Kits of the disclosure can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

5.1. Example 1

Assays

5.1.1. TNFα Inhibition Assay in PBMC

Peripheral blood mononuclear cells (PBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bioproducts, Woodland, Calif., USA), 2 mM L-glutamine, 100 U/mL penicillin, and 100 µg/mL streptomycin (Life Technologies).

PBMC ($2\times10^5$ cells) are plated in 96-well flat-bottom Costar tissue culture plates (Corning, N.Y., USA) in triplicate. Cells are stimulated with LPS (from *Salmonella abortus* equi, Sigma cat. no. L-1887, St. Louis, Mo., USA) at 1 ng/mL final in the absence or presence of compounds. Compounds provided herein are dissolved in DMSO (Sigma) and further dilutions are done in culture medium immediately before use. The final DMSO concentration in all assays can be about 0.25%. Compounds are added to cells 1 hour before LPS stimulation. Cells are then incubated for 18-20 hours at 37° C. in 5% $CO_2$, and supernatants are then collected, diluted with culture medium and assayed for TNFα levels by ELISA (Endogen, Boston, Mass., USA). $IC_{50}$s are calculated using non-linear regression, sigmoidal dose-response, constraining the top to 100% and bottom to 0%, allowing variable slope (GraphPad Prism v3.02). In two experiments, Compound A demonstrated an $IC_{50}$ of 10 and 85 nM.

5.1.2. IL-2 and MIP-3α Production by T Cells

PBMC are depleted of adherent monocytes by placing $1\times10^8$ PBMC in 10 mL complete medium (RPMI 1640 supplemented with 10% heat-inactivated fetal bovine serum, 2 mM L-glutamine, 100 U/mL penicillin, and 100 µg/mL streptomycin) per 10 cm tissue culture dish, in 37° C., 5% $CO_2$ incubator for 30-60 minutes. The dish is rinsed with medium to remove all non-adherent PBMC. T cells are purified by negative selection using the following antibody (Pharmingen) and Dynabead (Dynal) mixture for every $1\times10^8$ non-adherent PBMC: 0.3 mL Sheep anti-mouse IgG beads, 15 µL anti-CD16, 15 µL anti-CD33, 15 µL anti-CD56, 0.23 mL anti-CD19 beads, 0.23 mL anti-HLA class II beads, and 56 µL anti-CD14 beads. The cells and bead/antibody mixture is rotated end-over-end for 30-60 minutes at 4° C. Purified T cells are removed from beads using a Dynal magnet. Typical yield is about 50% T cells, 87-95% $CD3^+$ by flow cytometry.

Tissue culture 96-well flat-bottom plates are coated with anti-CD3 antibody OKT3 at 5 µg/mL in PBS, 100 µL per well, incubated at 37° C. for 3-6 hours, then washed four times with complete medium 100 µL/well just before T cells are added. Compounds are diluted to 20 times of final in a round bottom tissue culture 96-well plate. Final concentrations are about 10 µM to about 0.00064 µM. A 10 mM stock of compounds provided herein is diluted 1:50 in complete for the first 20× dilution of 200 µM in 2% DMSO and serially diluted 1:5 into 2% DMSO. Compound is added at 10 µl per 200 µl culture, to give a final DMSO concentration of 0.1%. Cultures are incubated at 37° C., 5% $CO_2$ for 2-3 days, and supernatants analyzed for IL-2 and MIP-3α by ELISA (R&D Systems). IL-2 and MIP-3α levels are normalized to the amount produced in the presence of an amount of a compound provided herein, and $EC_{50}$s calculated using non-linear regression, sigmoidal dose-response, constraining the top to 100% and bottom to 0%, allowing variable slope (GraphPad Prism v3.02).

5.1.3. Cell Proliferation Assay

Cell lines Namalwa, MUTZ-5, and UT-7 are obtained from the Deutsche Sammlung von Mikroorganismen and Zellkulturen GmbH (Braunschweig, Germany). The cell line KG-1 is obtained from the American Type Culture Collection (Manassas, Va., USA). Cell proliferation as indicated by $^3$H-thymidine incorporation is measured in all cell lines as follows.

Cells are plated in 96-well plates at 6000 cells per well in media. The cells are pre-treated with compounds at about 100, 10, 1, 0.1, 0.01, 0.001, 0.0001 and 0 µM in a final concentration of about 0.25% DMSO in triplicate at 37° C. in a humidified incubator at 5% $CO_2$ for 72 hours. One microcurie of $^3$H-thymidine (Amersham) is then added to each well, and cells are incubated again at 37° C. in a humidified incubator at 5% $CO_2$ for 6 hours. The cells are harvested onto UniFilter GF/C filter plates (Perkin Elmer) using a cell harvester (Tomtec), and the plates are allowed to dry overnight. Microscint 20 (Packard) (25 µL/well) is added, and plates are analyzed in TopCount NXT (Packard). Each well is counted for one minute. Percent inhibition of cell proliferation is calculated by averaging all triplicates and normalizing to the DMSO control (0% inhibition). Each compound is tested in each cell line in three separate experiments. Final $IC_{50}$s are calculated using non-linear regression, sigmoidal dose-response, constraining the top to 100% and bottom to 0%, allowing variable slope. (GraphPad Prism v3.02).

5.1.4. Immunoprecipitation and Immunoblot

Namalwa cells are treated with DMSO or an amount of a compound provided herein for 1 hour, then stimulated with 10 U/mL of Epo (R&D Systems) for 30 minutes. Cell lysates are prepared and either immunoprecipitated with Epo receptor Ab or separated immediately by SDS-PAGE. Immunoblots are probed with Akt, phospho-Akt (Ser473 or Thr308), phospho-Gab1 (Y627), Gab1, IRS2, actin and IRF-1 Abs and analyzed on a Storm 860 Imager using ImageQuant software (Molecular Dynamics).

5.1.5. Cell Cycle Analysis

Cells are treated with DMSO or an amount of a compound provided herein overnight. Propidium iodide staining for cell cycle is performed using CycleTEST PLUS (Becton Dickinson) according to manufacturer's protocol. Following staining, cells are analyzed by a FACSCalibur flow cytometer using ModFit LT software (Becton Dickinson).

5.1.6. Apoptosis Analysis

Cells are treated with DMSO or an amount of a compound provided herein at various time points, then washed with annexin-V wash buffer (BD Biosciences). Cells are incubated with annexin-V binding protein and propidium iodide (BD Biosciences) for 10 minutes. Samples are analyzed using flow cytometry.

5.1.7. Luciferase Assay

Namalwa cells are transfected with 4 µg of AP1-luciferase (Stratagene) per $1\times10^6$ cells and 3 µL Lipofectamine 2000

(Invitrogen) reagent according to manufacturer's instructions. Six hours post-transfection, cells are treated with DMSO or an amount of a compound provided herein. Luciferase activity is assayed using luciferase lysis buffer and substrate (Promega) and measured using a luminometer (Turner Designs).

5.2. Example 2

Preparation of 3-(5-Amino-2-Methyl-4-Oxo-4H-Quinazolin-3-Yl)-Piperidine-2,6-Dione (Compound A)

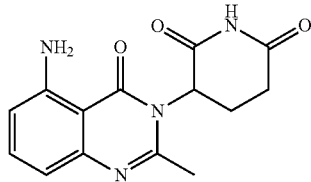 [SMILES: Cc1nc2cccc(N)c2c(=O)n1C1CCC(=O)NC1=O]

Step 1: To a solution of potassium hydroxide (16.1 g, 286 mmol) in water (500 mL), was added 3-nitrophthalimide (25.0 g, 130 mmol) in portion at 0° C. The suspension was stirred at 0° C. for 3 hrs, and then heated to 30° C. for 3 hrs. To the solution, was added HCl (100 mL, 6N). The resulting suspension was cooled to 0° C. for 1 hr. The suspension was filtered and washed with cold water (2×10 mL) to give 3-nitro-phthalamic acid as a white solid (24.6 g, 90% yield): $^1$H NMR (DMSO-$d_6$) δ 7.69 (brs, 1H, NHH), 7.74 (t, J=8 Hz, 1H, Ar), 7.92 (dd, J=1, 8 Hz, 1H, Ar), 8.13 (dd, J=1, 8 Hz, 1H, Ar), 8.15 (brs, 1H, NHH), 13.59 (s, 1H, OH); $^{13}$C NMR (DMSO-$d_6$) δ 125.33, 129.15, 130.25, 132.54, 136.72, 147.03, 165.90, 167.31.

Step 2: To a mixture of 3-nitro-phthalamic acid (24.6 g, 117 mmol) and potassium hydroxide (6.56 g, 117 mmol) in water (118 mL), was added a mixture of bromine (6 mL), potassium hydroxide (13.2 g, 234 mmol) in water (240 mL) at 0° C., followed by addition of a solution of potassium hydroxide (19.8 g, 351 mmol) in water (350 mL). After 5 minutes at 0° C., the mixture was heated in a 100° C. oil bath for 1 hr. The reaction solution was cooled to room temperature, and then, in an ice-water bath for 30 minutes. To the mixture, a solution of HCl (240 mL, 2N) was added dropwise at 0° C., and the resulting mixture was kept for 1 hr. The suspension was filtered and washed with water (5 mL) to give 2-amino-6-nitro-benzoic acid as yellow solid (15.6 g, 73% yield): HPLC: Waters Symmetry $C_{18}$, 5 μm, 3.9×150 mm, 1 mL/min, 240 nm, $CH_3CN/0.1\% H_3PO_4$, 5% grad to 95% over 5 min, 5.83 min (85%); $^1$H NMR (DMSO-$d_6$) δ 6.90 (dd, J=1, 8 Hz, 1H, Ar), 7.01 (dd, J=1, 9 Hz, 1H, Ar), 7.31 (t, J=8 Hz, 1H, Ar), 8.5-9.5 (brs, 3H, OH, $NH_2$); $^{13}$C NMR (DMSO-$d_6$) δ 105.58, 110.14, 120.07, 131.74, 149.80, 151.36, 166.30; LCMS: MH=183.

Step 3: A mixture of 2-amino-6-nitro-benzoic acid (1.5 g, 8.2 mmol) in acetic anhydride (15 mL) was heated at 200° C. for 30 minutes in a microwave oven. The mixture was filtered and washed with ethyl acetate (20 mL). The filtrate was concentrated in vacuo. The solid was stirred in ether (20 mL) for 2 hrs. The suspension was filtered and washed with ether (20 mL) to give 2-methyl-5-nitro-benzo[d][1,3]oxazin-4-one as a light brown solid (1.4 g, 85% yield): HPLC: Waters Symmetry $C_{18}$, 5 μm, 3.9×150 mm, 1 mL/min, 240 nm, $CH_3CN/0.1\% H_3PO_4$, 5% grad 95% in 5 min, 5.36 min (92%); $^1$H NMR (DMSO-$d_6$) δ 2.42 (s, 3H, $CH_3$), 7.79 (dd, J=1, 8 Hz, 1H, Ar), 7.93 (dd, J=1, 8 Hz, 1H, Ar), 8.06 (t, J=8 Hz, 1H, Ar); $^{13}$C NMR (DMSO-$d_6$) δ 20.87, 107.79, 121.54, 128.87, 137.19, 147.12, 148.46, 155.18, 161.78; LCMS: MH=207.

Step 4: Two vials each with a suspension of 5-nitro-2-methyl-benzo[d][1,3]oxazin-4-one (0.60 g, 2.91 mmol) and 3-amino-piperidine-2,6-dione hydrogen chloride (0.48 g, 2.91 mmol) in pyridine (15 mL) were heated at 170° C. for 10 minutes in a microwave oven. The suspension was filtered and washed with pyridine (5 mL). The filtrate was concentrated in vacuo. The resulting mixture was stirred in HCl (30 mL, 1N), ethyl acetate (15 mL) and ether (15 mL) for 2 hrs. The suspension was filtered and washed with water (30 mL) and ethyl acetate (30 mL) to give a dark brown solid, which was stirred with methanol (50 mL) at room temperature overnight. The suspension was filtered and washed with methanol to give 3-(2-methyl-5-nitro-4-oxo-4H-quinazolin-3-yl)-piperidine-2,6-dione as a black solid (490 mg, 27% yield). The solid was used in the next step without further purification.

Step 5: A mixture of 3-(2-methyl-5-nitro-4-oxo-4H-quinazolin-3-yl)-piperidine-2,6-dione (250 mg) and $Pd(OH)_2$ on carbon (110 mg) in DMF (40 mL) was shaken under hydrogen (50 psi) for 12 hrs. The suspension was filtered through a pad of Celite and washed with DMF (10 mL). The filtrate was concentrated in vacuo and the resulting oil was purified by flash column chromatography (silica gel, methanol/methylene chloride) to give 3-(5-amino-2-methyl-4-oxo-4H-quinazolin-3-yl)-piperidine-2,6-dione as a white solid (156 mg, 69% yield): HPLC: Waters Symmetry $C_{18}$, 5 μm, 3.9×150 mm, 1 mL/min, 240 nm, 10/90 $CH_3CN/0.1\% H_3PO_4$, 3.52 min (99.9%); mp: 293-295° C.; $^1$HNMR (DMSO-$d_6$) δ 2.10-2.17 (m, 1H, CHH), 2.53 (s, 3H, $CH_3$), 2.59-2.69 (m, 2H, $CH_2$), 2.76-2.89 (m, 1H, CHH), 5.14 (dd, J=6, 11 Hz, 1H, NCH), 6.56 (d, J=8 Hz, 1H, Ar), 6.59 (d, J=8 Hz, 1H, Ar), 7.02 (s, 2H, $NH_2$), 7.36 (t, J=8 Hz, 1H, Ar), 10.98 (s, 1H, NH); $^{13}$C NMR (DMSO-$d_6$) δ 20.98, 23.14, 30.52, 55.92, 104.15, 110.48, 111.37, 134.92, 148.17, 150.55, 153.62, 162.59, 169.65, 172.57; LCMS: MH=287; Anal. Calcd. for $C_{14}H_{14}N_4O_3$+0.3 $H_2O$: C, 57.65; H, 5.05; N, 19.21. Found: C, 57.50; H, 4.73; N, 19.00.

5.3. Example 3

Preparation of Compound A Hydrochloride

In a stirred glass flask, approximately 19 g of Compound A (freebase) was suspended in approximately 200 mL acetonitrile and 200 mL water. Approximately 5 mL 12 N hydrochloric acid was added, and the suspension was dissolved by heating above 55° C. The solution was cooled to approx 45° C. and seed crystals of Compound A Form A1 (e.g. Hydrochloride) were added to the flask. Then 6 N hydrochloric acid was added dropwise causing further crystallization. The slurry was slowly cooled. The slurry was then filtered and the cake was washed with acetonitrile. The product was then dried in a vacuum oven. The resulting dry product was consistent with Compound A Form A1.

5.4. Example 4

Solid Form Screening Studies

5.4.1. Experimental Methodology

The methods described herein are illustrated with Compound A hydrochloride. These methods can be used directly or with some modification for other solids forms of Compound A as described herein.

Solubility: A weighed sample of Compound A hydrochloride (about 50 mg) was treated with a known volume of a test solvent. The solvents used were either reagent or HPLC grade. The resulting mixture was agitated for at least 24 hours at about 25° C. If all of the solids appeared to be dissolved by visual inspection, the estimated solubilities were calculated based on the total volume of solvent used to give a complete solution. The actual solubilities may be greater than those calculated due to the use of large amount of solvent or to a slow rate of dissolution. If solids were present, the solubility was measured gravimetrically. A known volume of filtrate was evaporated to dryness and the weight of the residue was measured.

Equilibration/Slurry and Evaporation: Equilibration and evaporation experiments were carried out by adding an excess of Compound A hydrochloride to about 2 mL of a test solvent. The resulting mixture was agitated for at least 24 hrs at about 25° C. or about 50° C. Upon reaching equilibrium, the saturated solution was removed and allowed to evaporate slowly in an open vial under nitrogen at about 25° C. and about 50° C., respectively. The solids resulting from the equilibration were filtered and dried in the air.

Cooling Recrystallization: The selected solvents (THF/water, MeCN/water, MeOH/0.1N HCl, and EtOH/0.1N HCl) were saturated with Compound A hydrochloride at about 50-70° C. Once the solids were completely dissolved, the solution was rapidly cooled by placing into a refrigerator (about 0-5° C.). Solids were isolated after 1 to 3 days.

Solvent/Anti-Solvent Recrystallization: The selected solvent (MeCN/water) was saturated with Compound A hydrochloride at room temperature. Once the solids were completely dissolved, an anti-solvent (acetone or IPA) was added into the solution. The mixture was stirred at room temperature overnight. If no precipitation occurred, the vial was further cooled by placing into a refrigerator (about 0-5° C.). The solids resulting from the recrystallization were filtered and air-dried.

Grinding Studies: Grinding experiments were performed using a Wig-L-Bug shaker. About 50 mg of Compound A hydrochloride was added to a polystyrene tube (1"×½") with a Plexi bead (⅜"). The vial was capped and placed on the shaker for about 50 s. For wet grinding, drops of water were added to the vial and a wet paste was formed prior to placing on the shaker.

Humidity Studies: About 30 mg of Compound A hydrochloride was placed in amber glass vials in duplicate. The vials were placed in 40° C./75% RH humidity chamber with one vial capped and one vial open. The solids were tested by XRPD after four weeks. An additional humidity stress experiment was performed by placing about 10 mg of Compound A hydrochloride in a DVS instrument at 95% RH and room temperature for four days.

5.4.2. Characterization Methodology

X-ray Powder Diffraction (XRPD): XRPD analysis was conducted on a Thermo ARL X'TRA™ X-ray powder diffractometer using Cu Kα radiation at 1.54 Å. The instrument was equipped with a fine focus X-ray tube. The voltage and amperage of X-ray generator were set at 45 kV and 40 mA, respectively. The divergence slices were set at 4 mm and 2 mm and the measuring slices were set at 0.5 mm and 0.2 mm. Diffracted radiation was detected by a peltier-cooled Si(Li) solid-state detector. A theta-two theta continuous scan at 2.40°/min (0.5 sec/0.02° step) from 1.5 °2θ to 40 °2θ was used. A sintered alumina standard was used to check the peak position. In general, positions of XRPD peaks are expected to individually vary on a measurement-by-measurement basis by about ±0.2 °2θ. In general, as understood in the art, two XRPD patterns match one another if the characteristic peaks of the first pattern are located at approximately the same positions as the characteristic peaks of the second pattern. As understood in the art, determining whether two XRPD patterns match or whether individual peaks in two XRPD patterns match may require consideration of individual variables and parameters such as, but not limited to, preferred orientation, phase impurities, degree of crystallinity, particle size, variation in diffractometer instrument setup, variation in XRPD data collection parameters, and/or variation in XRPD data processing, among others. The determination of whether two patterns match may be performed by eye and/or by computer analysis.

Differential Scanning calorimetry (DSC): DSC analyses were performed on a TA Instruments Q2000™ differential scanning calorimeter. Indium was used as a calibration standard. About 2-5 mg of a sample was placed in to a DSC pan. The sample was heated under nitrogen at a rate of 10° C./min from about 25° C. up to a final temperature of 300° C. Melting points were reported as the extrapolated onset temperatures.

Thermal Gravimetric Analyses (TGA): TGA analyses were performed on a TA Instruments Q5000™ thermogravimetric analyzer. Calcium oxalate was used for calibration. About 5-20 mg of an accurately weighted sample was placed on a pan, and loaded into the TGA furnace. The sample was heated under nitrogen at a rate of about 10° C./min up to a final temperature of about 300° C.

Optical Microscopy: Morphology analysis of a sample was carried out on an Olympus microscope. Small amounts of a sample were dispersed in mineral oil on a glass slide with cover slips and viewed with 20× magnification.

Dynamic Vapor Sorption (DVS): Hygroscopicity was determined on a Surface Measurement Systems DVS. Typically, a sample of about 2-10 mg was loaded into the DVS instrument sample pan. The sample was analyzed on a DVS automated sorption analyzer at room temperature. The relative humidity was increased from 0 to 95% RH at 10% RH step, then at 95% RH. The relative humidity was then decreased in a similar manner to accomplish a full adsorption/desorption cycle.

Solubility by HPLC: Solubility of Form A in selected aqueous and organic solvents was determined by mixing solid with solvents at room temperature. The samples were filtered after 24 hr of agitation and quantified by an HPLC method, except for DMSO, for which the solubility was measured after 1 hr of agitation.

5.4.3. Solid Form Screening Study Results

Solid forms comprising Compound A which were prepared during the solid form screening studies included Form A, B, C, D, E, F, and A1, and amorphous forms. Representative XRPD patterns, DSC plots, TGA plots and DVS plots for Form A, B, C, D, E, F, and I are provided herein as FIGS. 1 to 21.

5.4.3.1. Solid Forms of Compound A

Figure 23:
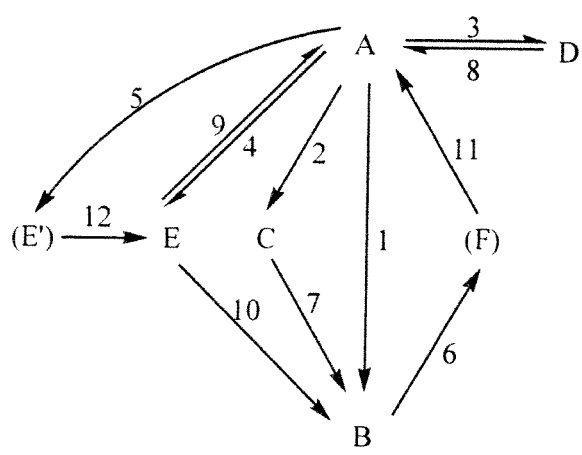
FIG. 23 depicts interconversions between various solid forms of 3-(5-amino-2-methyl-4-oxo-4H-quinazolin-3-yl)-piperidine-2,6-dione.

Interconversions between various solid forms of Compound A are summarized in FIG. 23. The interconversion conditions as depicted in FIG. 23 are:

1. Slurry in MeOH at RT, or in acetone, MeCN, or MeOH at 50° C.
2. Slurry in EtOAC, EtOH, IPA, MEK, n-BuOH or THF at 50° C.

3. Dried in vacuum oven at ~70° C.
4. Slurry in MeCN or IPA at RT
5. Slurry in EtOH at RT
6. Slurry in water at RT
7. Slurry in organic solvents at RT or elevated temperature
8. Exposure to moisture at RT
9. Slurry in water at RT
10. Slurry in organic solvents at elevated temperature
11. Slurry in water at RT
12. Exposure to moisture in DVS The physical properties of Forms A, B, C, D, E, and F are summarized in Table 2.

TABLE 2

Characteristics of Solid Forms of Compound A

| Form | Morphology | DSC Peaks (° C.) | TGA Loss (wt %) | Moisture Sorption at 95% RH (wt %) | Comment |
|---|---|---|---|---|---|
| A | Crystalline Irregular plate | 145.3 (broad) 161.2 (exo) 282.1 (onset) | 5.87 | 3.19 | Mono-hydrate |
| B | Crystalline Irregular shape | 279.0 (onset) | 0.00 | 0.11 | Anhydrate |
| C | Crystalline Irregular shape | 280.7 (onset) | 0.07 | 0.17 | Anhydrate |
| D | Semi-crystalline Irregular shape | 114.4 (broad) 283.3 (onset) | 3.04 | 4.11 | Unstable dehydrated form |
| E | Crystalline Large irregular plate | 147.0 (broad) 279.4 (onset) | 5.98 | 0.26 | Hydrate/solvate |
| F | Crystalline | 170.4 (exo) 266.5 (onset) | | | |

In a stirred glass flask, 3.5 g Compound A freebase was dissolved in approx 14 mL DMSO and approx 0.7 mL water at room temperature. Approx 2 mL water was added and crystals of Compound A Form A began to form. Additional water was added dropwise and the batch further crystallized. The batch was then filtered. The cake was washed with a 1:1 (v:v) DMSO:water solution and neat water. The wet cake was dried in a vacuum oven. The final dry product was consistent with Compound A Form A.

Alternatively, Compound A Form A can be obtained by seeding. In a stirred glass flask, 3.5 g Compound A freebase was dissolved in approx 14 mL DMSO and approx 0.7 mL water at room temperature. Approx 1.3 mL water was added, and seeds of Compound A Form A were added, and the batch began to crystallize. Additional water was added dropwise, and the batch further crystallized. The batch was then filtered. The cake was then washed with 1:1 (v:v) DMSO:water solution and neat water. The wet cake was dried in a vacuum oven. The final dry product was consistent with Compound A Form A.

Form B of Compound A was prepared from Form A via slurry recrystallization in methanol, acetone or acetonitrile. The slurry experiments were carried out by adding an excess of Compound A to 2 mL of methanol, acetone or acetonitrile. The resulting mixture was agitated for at least 24 hours at about 50° C. Upon reaching equilibrium, the solid was filtered and air dried.

Form C of Compound A was prepared from Form A via slurry recrystallization in EtOAc, EtOH, IPA, MEK, n-BuOH, or THF at about 50° C. The slurry experiments were carried out by adding an excess of Compound A to 2 mL of EtOAc, EtOH, IPA, MEK, n-BuOH, or THF. The resulting mixture was agitated for at least 24 hours at about 50° C. Upon reaching equilibrium, the solid was filtered and air dried.

Form D of Compound A was prepared from Form A via drying Form A in vacuum oven at about 80-90° C.

Form E of Compound A was prepared from Form A via slurry recrystallization in acetonitrile, ethanol or isopropanol at room temperature. The slurry experiments were carried out by adding an excess of Compound A to 2 mL of acetonitrile, ethanol or isopropanol. The resulting mixture was agitated for at least 24 hours at room temperature. Upon reaching equilibrium, the solid was filtered and air dried.

Form F of Compound A was prepared from Form B via slurry recrystallization in water at room temperature. The slurry experiment was carried out by adding an excess of Compound A to 2 mL of water. The resulting mixture was agitated for at least 16 hours at room temperature. The solid was then filtered and air dried.

5.4.3.2. Solid Form A1 of Compound A HCl

Form A1, a hydrochloride salt of Compound A was prepared by the following process. In a stirred glass flask, 2 g Compound A hydrochloride was mixed in a solvent mixture of approximately 20 mL acetonitrile and 20 mL water and dissolved by heating to >55° C. The solution was cooled to 45° C. and approx 3.3 mL 6 N hydrochloric acid was added, causing crystallization. The slurry was then slowly cooled and filtered. The cake was washed with acetonitrile and then dried in a vacuum oven. The resulting dry product was consistent with Compound A Form A1.

Large Scale Process.

Form A1 was prepared on a large scale by combining 100 g of Compound A hydrochloride, 960 mL acetonitrile and 960 mL deionized water in a reactor. The mixture was heated with agitation to 60 to 70° C. and transferred to a second reactor by an inline filter (0.45 µm). The first reactor is rinsed with 100 mL of acetonitrile:water (1:1), which was transferred to the second reactor by the inline filter. The temperature in the second reactor was maintained at 65° C. during transfer. The second reactor was then cooled to 45° C. and seeded with 3 g Form A1 crystals. The batch began to crystallize and was aged at 45° C. for 30 minutes. To the resulting slurry was added 171 mL 6 N HCl by an inline filter over 1 hour, maintaining batch temperature at about 45° C. The batch was aged at 45° C. for 1.5 hours and cooled to 0° C. in a linear ramp over 4 hours. The batch was then aged at 0° C. for 1 hour. The supernatant was sampled for UPLC concentration. The concentration of Form A1 in the supernatant was 5 mg/mL. The slurry was filtered through a fritted glass filter with vacuum. The resulting cake was displacement washed with 2×300 mL acetonitrile washes. The cake was dried in a vacuum oven at 40° C. until acetonitrile is <400 ppm. The dry cake of Form A1 was a clean white/off-white powder.

It was discovered that acetonitrile:water was the only solvent system which afforded acceptable properties for scaleup, e.g., solubility greater than about 50 g/mL product. Excess HCl was added to prevent formation of the free base of Compound A. In some cases it was found that the absence of HCl in the process resulted in free base formation. Excess HCl was also thought to improve Form A1 yield during crystallization.

The physical properties from the HCl salt are consistent from batch to batch. TGA shows little residual solvent (also, by NMR residual acetonitrile can be reduced to <400 ppm). DSC shows a single event at ~280° C., which is considered to be decomposition (similar to the decomposition point of the freebase). Microscopy showed long rod morphology.

Solubility Studies.

The approximate solubility of Form A1 of Compound A hydrochloride in various solvents at about 25° C. was determined. Form A1 was found to be most soluble (>25 mg/mL) in MeCN/water (1:1) and THF/water (1:1). Form A1 was found to have moderate solubility (3-10 mg/mL) in EtOH/water (1:1), MeOH, $CH_2Cl_2$, THF, and water. Form A1 was found to have low solubility (<3 mg/mL) in other organic solvents tested. The solubility of Form A1 in selected solvents was also tested by HPLC and results are shown in Table 3.

TABLE 3

| Solubility | |
| --- | --- |
| Solvent | Solubility (mg/mL) |
| Water | 1.71 |
| 0.9% NaCl | 1.90 |
| 0.1N HCl | 5.34 |
| Acetate buffer (pH 4.0) | 0.31 |
| Phosphate buffer (pH 6.8) | 0.03 |
| Acetonitrile (AcCN) | 0.02 |
| Acetone | 2.55 |
| Methanol (MeOH) | 0.27 |
| Isopropanol (iPrOH) | 0.02 |
| Ethyl acetate (EtOAc) | <0.001 |
| Tetrahydrofuran (THF) | <0.005 |
| Heptane | <0.001 |
| Toluene | <0.005 |
| Dimethyl Sulfoxide (DMSO) | 21.88 |

Slurry experiments were performed at room temperature and 50° C. using Form A1 of Compound A hydrochloride as starting material. The results are summarized in Tables 4 and 5. All of the solids isolated from pure organic solvents after 24 hrs of slurry were confirmed to be Form A1 by XRPD. The solid isolated from THF/water at 50° C. slurry was also confirmed to be Form A1. The solids isolated from other aqueous/organic or aqueous slurries were shown be to mixtures of Form A1 and Compound A free base, suggesting partial dissociation of the HCl salt.

TABLE 4

| Equilibration Experiments at Room Temperature. | |
| --- | --- |
| Solvent | XRPD Result |
| Acetone | Form A1 |
| Acetonitrile | Form A1 |
| n-Butanol | Form A1 |
| Ethanol | Form A1 |
| Ethyl acetate | Form A1 |
| Heptane | Form A1 |
| Methanol | Form A1 |
| Methylene chloride | Form A1 |
| Methyl ethyl ketone | Form A1 |
| Methyl t-butyl ether | Form A1 |
| 2-Propanol | Form A1 |
| Toluene | Form A1 |
| Tetrahydrofuran | Form A1 |
| Water | Form A + Form A1 |
| Ethanol/Water (1:1) | Form A + Form A1 |
| Acetonitrile/Water (1:1) | Form A + Form A1 |
| Tetrahydrofuran/Water (1:1) | Form A + Form A1 |

TABLE 5

| Equilibration Experiments at 50° C. | |
| --- | --- |
| Solvent | XRPD Result |
| Acetone | Form A1 |
| Acetonitrile | Form A1 |
| n-Butanol | Form A1 |
| Ethanol | Form A1 |
| Ethyl acetate | Form A1 |
| Heptane | Form A1 |
| Methanol | Form A1 |
| Methyl ethyl ketone | Form A1 |
| 2-Propanol | Form A1 |
| Toluene | Form A1 |
| Tetrahydrofuran | Form A1 |
| Water | Form A + Form A1 |
| Ethanol/Water (1:1) | Form A + Form A1 |
| Acetonitrile/Water (1:1) | Form A + Form A1 |
| Tetrahydrofuran/Water (1:1) | Form A1 |

Evaporation experiments were performed. The results are summarized in Tables 6 and 7. For room temperature evaporations, solids obtained from water, EtOH/water, and MeCN/water were confirmed to be Form A1. Partial or complete salt dissociation were observed in MeOH, THF, and THF/water. For 50° C. evaporations, solids obtained from MeOH, water, EtOH/water, and MeCN/water were confirmed to be Form A1. Solid from THF/water was shown to be amorphous.

TABLE 6

| Evaporation Experiments at Room Temperature | |
| --- | --- |
| Solvent | XRPD Result |
| Acetone | N/A |
| Acetonitrile | N/A |
| n-Butanol | N/A |
| Ethanol | N/A |
| Ethyl acetate | N/A |
| Heptane | N/A |
| Methanol | Form A + Form A1 |
| Methyl ethyl ketone | N/A |
| 2-Propanol | N/A |
| Toluene | N/A |
| Tetrahydrofuran | N/A |
| Water | Form A1 |
| Ethanol/Water (1:1) | Form A1 |
| Acetonitrile/Water (1:1) | Form A1 |
| Tetrahydrofuran/Water (1:1) | Form A + Form A1 |

TABLE 7

| Evaporation Experiments at 50° C. | |
| --- | --- |
| Solvent | XRPD Result |
| Acetone | N/A |
| Acetonitrile | N/A |
| n-Butanol | N/A |
| Ethanol | N/A |
| Ethyl acetate | N/A |
| Heptane | N/A |
| Methanol | Form A1 |
| Methyl ethyl ketone | N/A |
| 2-Propanol | N/A |
| Toluene | N/A |
| Tetrahydrofuran | N/A |
| Water | Form A1 |
| Ethanol/Water (1:1) | Form A1 |
| Acetonitrile/Water (1:1) | Form A1 |
| Tetrahydrofuran/Water (1:1) | Amorphous |

Recrystallization experiments were performed in several organic/aqueous mixtures. The results are summarized in Table 8. Solids from MeCN/water, MeOH/0.1N HCl, or EtOH/0.1N HCl were confirmed to be Form A1. Complete salt dissociation was observed in THF/water.

Anti-solvent crystallization was also performed with MeCN/water as the primary solvent system, and with acetone or IPA as antisolvent. Form A1 was obtained when acetone was used as antisolvent, and partial salt dissociation was observed when IPA was used as antisolvent.

TABLE 8

Recrystallization without and with Antisolvents

| Solvent | Antisolvent | Ratio (Solvent/Antisolvent) | XRPD Result |
| --- | --- | --- | --- |
| THF/H$_2$O | NA | NA | Form A |
| MeCN/H$_2$O | NA | NA | Form A1 + Form A |
| MeOH/0.1N HCl | NA | NA | Form A1 |
| EtOH/0.1N HCl | NA | NA | Form A1 |
| MeCN/H$_2$O | Acetone | 1:5 | Form A1 |
| MeCN/H$_2$O | IPA | 1:5 | Form A1 + Form A |

Grinding experiments were performed with and without addition of water, as a further attempt to generate polymorphs. Form A1 was found unchanged upon grinding. The results are summarized in Table 9.

TABLE 9

Grinding Experiments

| Starting Form | Test Conditions | XRPD Result |
| --- | --- | --- |
| Form A | Dry grinding | Form A1 |
| Form A | Wet grinding (paste) | Form A1 |

Characterization of Form A1

Figure 18:
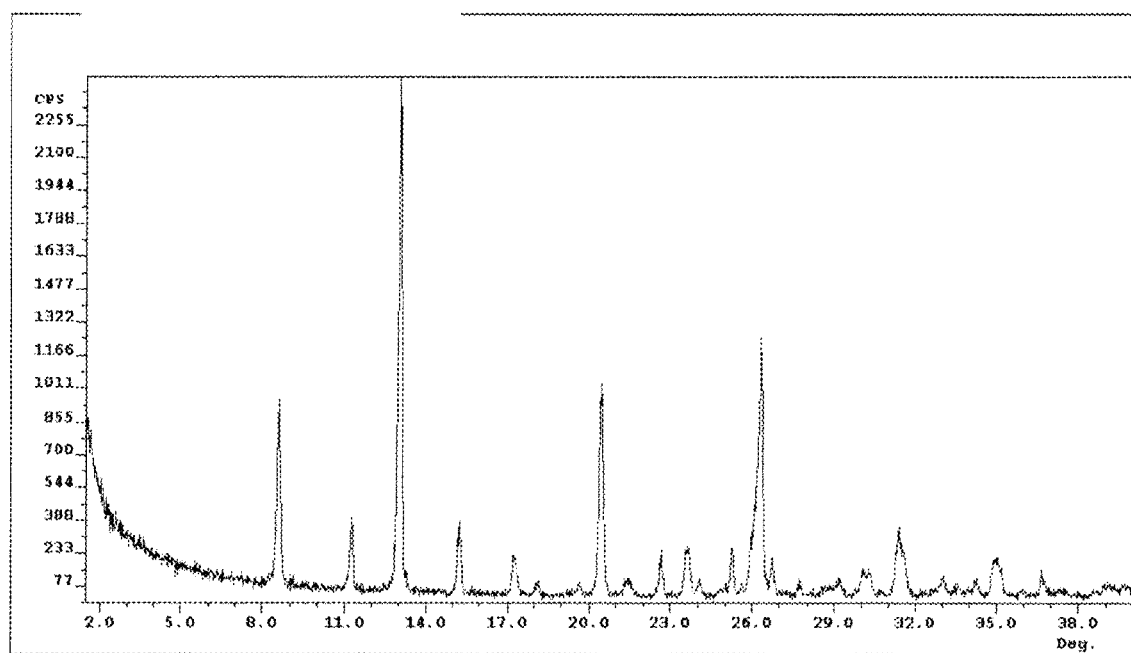

Form A1 had a crystalline XRPD pattern as shown in FIG. 18 and acicular crystal habit. TGA and DSC thermograms of Form A1 are shown in FIGS. 19 and 20, respectively. Negligible weight loss was observed prior to decomposition, the onset temperature of which was about 276° C. as determined by DSC.

The moisture sorption/desorption behavior of Form A1 was determined by DVS and the results are summarized in FIG. 21. Form A1 exhibited a 0.15% mass change relative to the dry mass when the relative humidity was increased from 0 to 95%, indicating that the material is non-hygroscopic. After undergoing the full adsorption/desorption cycle, the XRPD diffractogram of the sample showed that the material was unchanged from the initial Form A1.

Stability of Form A1 was determined by exposing the sample to a 40° C./75% RH environment for four weeks or 95% RH at room temperature for four days. Solid form of the exposed material was not changed compared to the initial unexposed sample (Table 10). Form A1 was also found to be stable upon application of 2000-psi pressure for about 1 minute.

TABLE 10

Grinding Experiments

| Starting Form | Test Conditions | XRPD Result |
| --- | --- | --- |
| Form A1 | 40° C./75% RH for 4 weeks, open vial | Form A1 |
| Form A1 | 40° C./75% RH for 4 weeks, closed vial | Form A1 |
| Form A1 | 95% RH for 4 days | Form A1 |

Based on these characterization studies, Form A1 was found to be a stable anhydrous and non-hygroscopic crystalline material.

While the disclosure has been described with respect to the particular embodiments, it will be apparent to those skilled in the art that various changes and modifications may be made without departing from the spirit and scope of the disclosure as defined in the claims. Such modifications are also intended to fall within the scope of the appended claims.

All of the patents, patent applications and publications referred to herein are incorporated herein in their entireties. Citation or identification of any reference in this application is not an admission that such reference is available as prior art to this disclosure. The full scope of the disclosure is better understood with reference to the appended claims.

Figure 4:
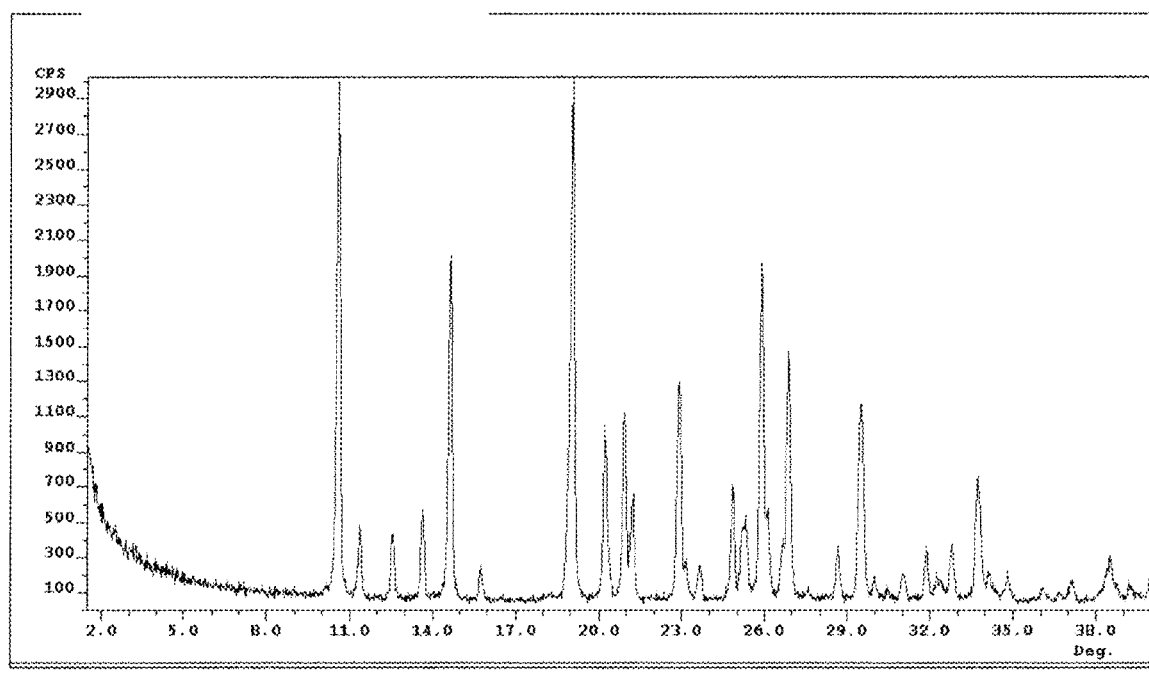
Figure 7:
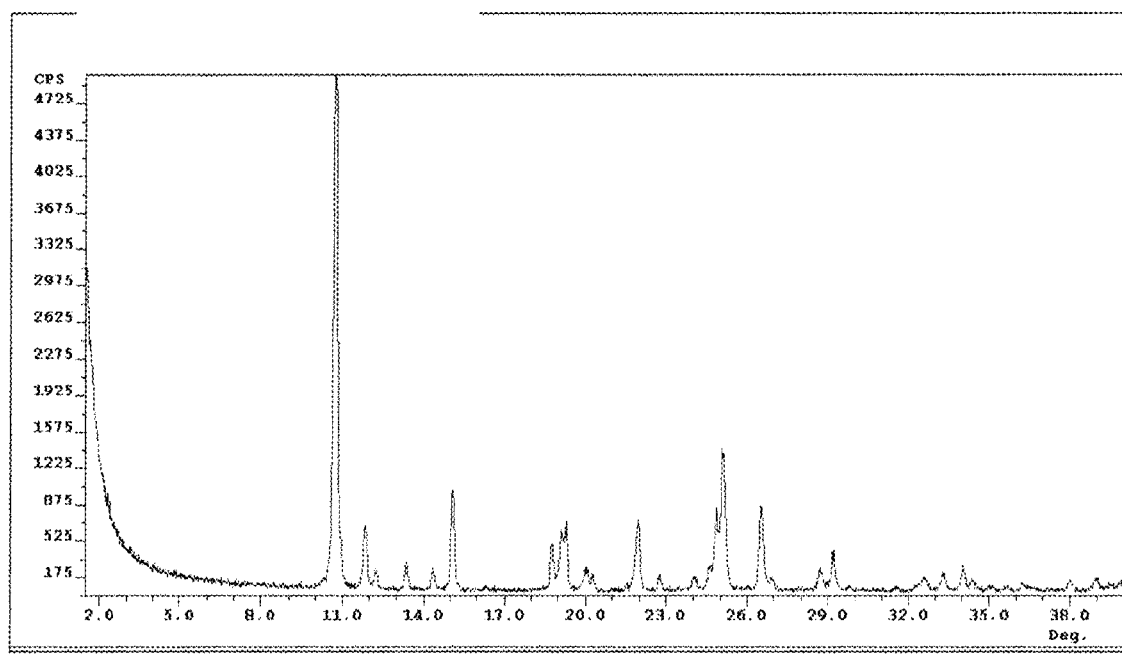
Figure 10:
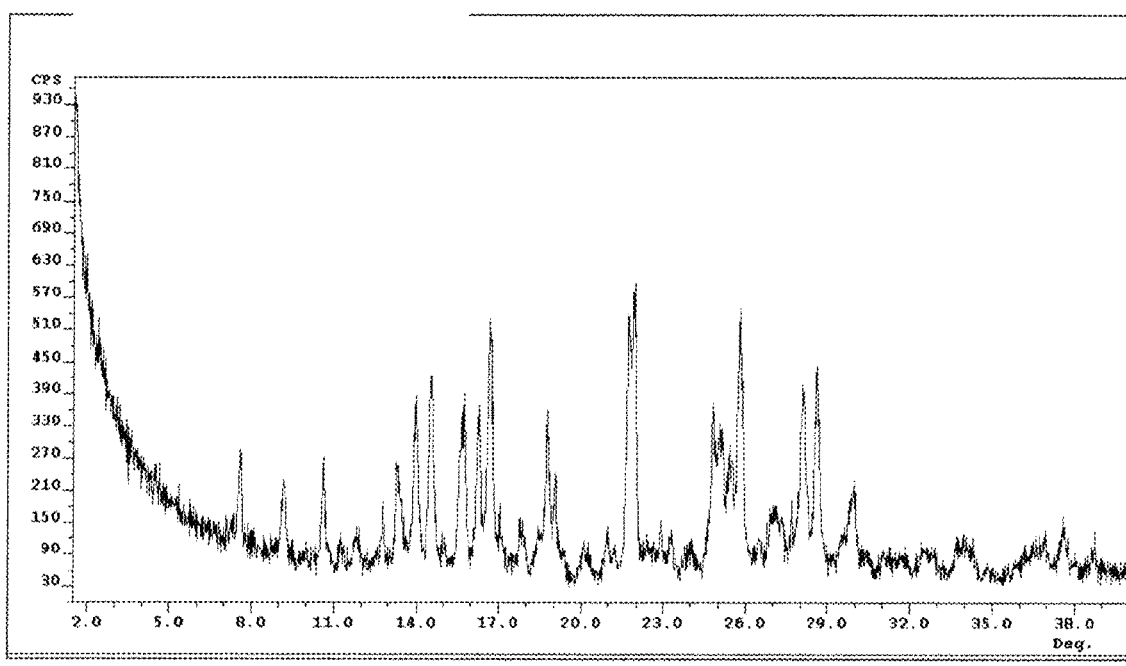
Figure 13:
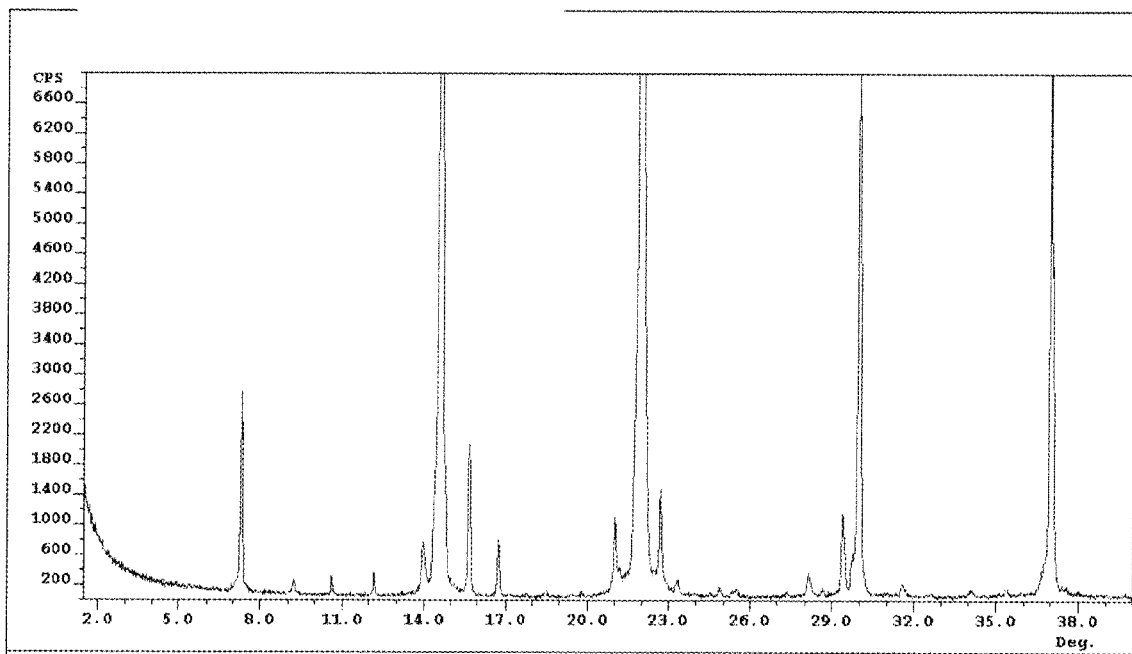
Figure 16:
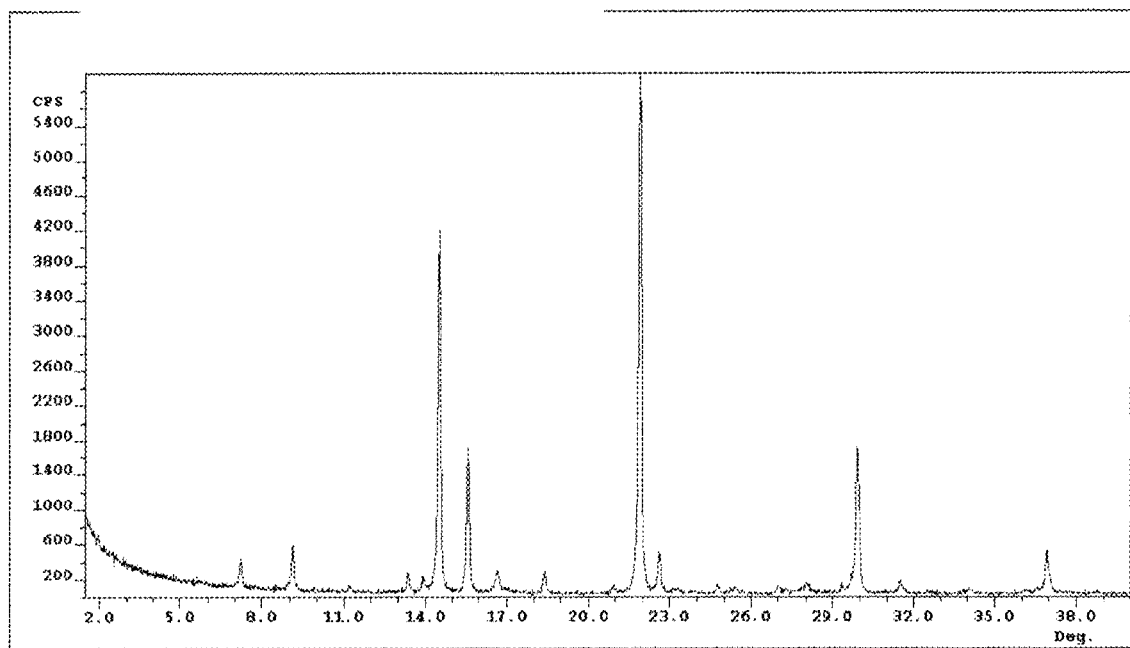

What is claimed is:

1. A method of treating inhibiting TNFα in a patient suffering from a disease or disorder comprising administering to the patient a solid form of 3-(5-amino-2-methyl-4-oxo-4H-quinazolin-3-yl)-piperidine-2,6-dione:

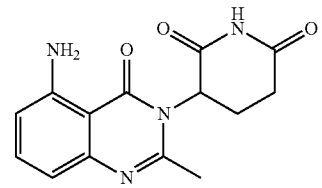 [SMILES: Cc1nc2cccc(N)c2c(=O)n1C1CCC(=O)NC1=O]

or a stereoisomer thereof, or a pharmaceutically acceptable salt, solvate, hydrate, co-crystal, or clathrate thereof; wherein the disease or disorder is cancer, a disorder associated with angiogenesis, pain, macular degeneration or a related syndrome, a skin disease, a pulmonary disorder, an asbestos-related disorder, a parasitic disease, an immunodeficiency disorder, a CNS disorder, CNS injury, atherosclerosis or a related disorder, dysfunctional sleep or a related disorder, hemoglobinopathy or a related disorder, or a TNFα related disorder; and wherein the solid form has an X-ray powder diffraction pattern comprising:
  peaks at approximately 14.6° 2θ, 15.6° 2θ, 16.7° 2θ, 21.9° 2θ and 30.0° 2θ as shown in FIG. 1;
  peaks at approximately 10.6° 2θ, 14.7° 2θ, 19.1° 2θ and 25.9° 2θ as shown in FIG. 4;
  peaks at approximately 10.8° 2θ, 15.1° 2θ, 25.1° 2θ and 26.6° 2θ as shown in FIG. 7;
  peaks at approximately 16.7° 2θ, 21.7° 2θ, 21.9° 2θ and 25.8° 2θ as shown in FIG. 10;
  peaks at approximately 7.3° 2θ, 14.6° 2θ, 22.0° 2θ, 30.0° 2θ and 37.0° 2θ as shown in FIG. 13;
  peaks at approximately 14.5° 2θ, 15.7° 2θ, 22.7° 2θ and 29.9° 2θ as shown in FIG. 16; or
  peaks at approximately 8.6° 2θ, 13.1° 2θ, 20.5° 2θ and 26.3° 2θ as shown in FIG. 18;
when analyzed using Cu Kα X-ray radiation at 1.54 Å.

2. The method of claim 1, wherein the solid form is a solid form of a hydrochloride salt of 3-(5-amino-2-methyl-4-oxo-4H-quinazolin-3-yl)-piperidine-2,6-dione, having an X-ray powder diffraction pattern comprising peaks at approximately 8.6° 2θ, 13.1° 2θ, 20.5° 2θ and 26.3° 2θ as shown in FIG. 18, when analyzed using Cu Kα X-ray radiation at 1.54 Å.

3. The method of claim 1, wherein the solid form has an X-ray powder diffraction pattern comprising peaks at approximately 8.6° 2θ, 11.3° 2θ, 13.1° 2θ, 15.3° 2θ, 17.3° 2θ, 20.5° 2θ, 22.7° 2θ, 23.6° 2θ, 26.3° 2θ and 31.4° 2θ as shown in FIG. 18, when analyzed using Cu Kα X-ray radiation at 1.54 Å.

4. The method of claim 2, wherein the solid form has a differential scanning calorimetry plot comprising an endothermic event with an onset temperature of approximately 276° C., when heated from approximately 25° C. to approximately 300° C.

5. The method of claim 2, wherein the solid form has a thermal gravimetric analysis plot comprising a mass loss of less than approximately 0.5% when heated from approximately 25° C. to approximately 150° C.

6. The method of claim 2, wherein the solid form is anhydrous.

7. The method of claim 2, wherein the solid form exhibits a mass increase of less than approximately 0.5% when subjected to an increase in relative humidity from approximately 0% to approximately 95% relative humidity.

8. The method of claim 2, wherein the solid form is substantially nonhygroscopic.

9. The method of claim 2, wherein the solid form is stable upon exposure to approximately 40° C. and approximately 75% relative humidity for approximately 4 weeks.

10. The method of claim 2, wherein the molar ratio of 3-(5-amino-2-methyl-4-oxo-4H-quinazolin-3-yl)-piperidine-2,6-dione to hydrochloride is from approximately 0.1 to approximately 10.

11. The method of claim 1, wherein the solid form has an X-ray powder diffraction pattern comprising peaks at approximately 14.6° 2θ, 15.6° 2θ, 16.7° 2θ, 21.9° 2θ and 30.0° 2θ as shown in FIG. 1, when analyzed using Cu Kα X-ray radiation at 1.54 Å.

12. The method of claim 1, wherein the solid form has an X-ray powder diffraction pattern comprising peaks at approximately 9.2° 2θ, 13.4° 2θ, 14.0° 2θ, 14.6° 2θ, 15.6° 2θ, 16.7° 2θ, 18.5° 2θ, 21.9° 2θ, 22.7° 2θ, 24.8° 2θ, 28.1° 2θ, 30.0° 2θ and 37.0° 2θ as shown in FIG. 1, when analyzed using Cu Kα X-ray radiation at 1.54 Å.

13. The method of claim 11, wherein the solid form has a differential scanning calorimetry plot comprising an endothermic event with an onset temperature of approximately 282° C., when heated from approximately 25° C. to approximately 300° C.

14. The method of claim 11, wherein the solid form has a thermal gravimetric analysis plot comprising a mass loss of less than approximately 6% when heated from approximately 25° C. to approximately 150° C.

15. The method of claim 11, wherein the solid form exhibits a mass increase of less than or equal to approximately 6% when subjected to an increase in relative humidity from approximately 0% to approximately 95% relative humidity.

16. The method of claim 11, wherein the solid form is hydrated.

17. The method of claim 16, wherein the crystal lattice of the solid form comprises approximately one molar equivalent of water per mole of 3-(5-amino-2-methyl-4-oxo-4H-quinazolin-3-yl)-piperidine-2,6-dione.

18. The method of claim 1, wherein the solid form has an X-ray powder diffraction pattern comprising peaks at approximately 10.6° 2θ, 14.7° 2θ, 19.1° 2θ and 25.9° 2θ as shown in FIG. 4, when analyzed using Cu Kα X-ray radiation at 1.54 Å.

19. The method of claim 1, wherein the solid form has an X-ray powder diffraction pattern comprising peaks at approximately 10.6° 2θ, 11.4° 2θ, 12.6° 2θ, 13.7° 2θ, 14.7° 2θ, 19.1° 2θ, 20.3° 2θ, 20.9° 2θ, 21.2° 2θ, 22.9° 2θ, 24.9° 2θ, 25.3° 2θ, 25.9° 2θ, 26.9° 2θ, 29.5° 2θ and 33.8° 2θ as shown in FIG. 4, when analyzed using Cu Kα X-ray radiation at 1.54 Å.

20. The method of claim 18, wherein the solid form has a differential scanning calorimetry plot comprising an endothermic event with an onset temperature of approximately 279° C., when heated from approximately 25° C. to approximately 300° C.

21. The method of claim 18, wherein the solid form has a thermal gravimetric analysis plot comprising a mass loss of less than approximately 0.1% when heated from approximately 25° C. to approximately 150° C.

22. The method of claim 18, wherein the solid form exhibits a mass increase of less than approximately 0.2% when subjected to an increase in relative humidity from approximately 0% to approximately 95% relative humidity.

23. The method of claim 18, wherein the solid form is unsolvated.

24. The method of claim 18, wherein the solid form is substantially nonhygroscopic.

25. The method of claim 1, wherein the solid form has an X-ray powder diffraction pattern comprising peaks at approximately 10.8° 2θ, 15.1° 2θ, 25.1° 2θ and 26.6° 2θ as shown in FIG. 7, when analyzed using Cu Kα X-ray radiation at 1.54 Å.

26. The method of claim 1, wherein the solid form has an X-ray powder diffraction pattern comprising peaks at approximately 10.8° 2θ, 11.9° 2θ, 15.1° 2θ, 18.8° 2θ, 19.2° 2θ, 19.3° 2θ, 22.0° 2θ, 24.9° 2θ, 25.1° 2θ, 26.6° 2θ and 29.2° 2θ as shown in FIG. 7, when analyzed using Cu Kα X-ray radiation at 1.54 Å.

27. The method of claim 25, wherein the solid form has a differential scanning calorimetry plot comprising an endothermic event with an onset temperature of approximately 281° C., when heated from approximately 25° C. to approximately 300° C.

28. The method of claim 25, wherein the solid form has a thermal gravimetric analysis plot comprising a mass loss of less than approximately 0.1% when heated from approximately 25° C. to approximately 150° C.

29. The method of claim 25, wherein the solid form exhibits a mass increase of less than approximately 0.2% when subjected to an increase in relative humidity from approximately 0% to approximately 95% relative humidity.

30. The method of claim 25, wherein the solid form is unsolvated.

31. The method of claim 25, wherein the solid form is substantially nonhygroscopic.

32. The method of claim 1, wherein the solid form has an X-ray powder diffraction pattern comprising peaks at approximately 16.7° 2θ, 21.7° 2θ, 21.9° 2θ and 25.8° 2θ as shown in FIG. 10, when analyzed using Cu Kα X-ray radiation at 1.54 Å.

33. The method of claim 1, wherein the solid form has an X-ray powder diffraction pattern comprising peaks at approximately 10.6° 2θ, 14.0° 2θ, 14.6° 2θ, 15.7° 2θ, 16.3° 2θ, 16.7° 2θ, 18.8° 2θ, 21.7° 2θ, 21.9° 2θ, 24.8° 2θ, 25.1° 2θ, 25.8° 2θ, 28.1° 2θ and 28.6° 2θ as shown in FIG. 10, when analyzed using Cu Kα X-ray radiation at 1.54 Å.

34. The method of claim 32, wherein the solid form has a differential scanning calorimetry plot comprising an endothermic event with an onset temperature of approximately 283° C., when heated from approximately 25° C. to approximately 300° C.

35. The method of claim 32, wherein the solid form has a thermal gravimetric analysis plot comprising a mass loss of less than approximately 4% when heated from approximately 25° C. to approximately 150° C.

36. The method of claim 32, wherein the solid form exhibits a mass increase of less than or equal to approximately 6% when subjected to an increase in relative humidity from approximately 0% to approximately 95% relative humidity.

37. The method of claim 1, wherein the solid form has an X-ray powder diffraction pattern comprising peaks at approximately 7.3° 2θ, 14.6° 2θ, 22.0° 2θ, 30.0° 2θ and 37.0° 2θ as shown in FIG. 13, when analyzed using Cu Kα X-ray radiation at 1.54 Å.

38. The method of claim 1, wherein the solid form has an X-ray powder diffraction pattern comprising peaks at approximately 7.3° 2θ, 9.3° 2θ, 12.2° 2θ, 14.0° 2θ, 14.6° 2θ, 15.7° 2θ, 16.8° 2θ, 21.0° 2θ, 22.0° 2θ, 22.7° 2θ, 29.4° 2θ, 30.0° 2θ and 37.0° 2θ as shown in FIG. 13, when analyzed using Cu Kα X-ray radiation at 1.54 Å.

39. The method of claim 37, wherein the solid form has a differential scanning calorimetry plot comprising an endothermic event with an onset temperature of approximately 279° C., when heated from approximately 25° C. to approximately 300° C.

40. The method of claim 37, wherein the solid form has a thermal gravimetric analysis plot comprising a mass loss of less than approximately 6% when heated from approximately 25° C. to approximately 150° C.

41. The method of claim 37, wherein the solid form exhibits a mass increase of less than approximately 0.5% when subjected to an increase in relative humidity from approximately 0% to approximately 95% relative humidity.

42. The method of claim 37, wherein the solid form is hydrated.

43. The method of claim 37, wherein the solid form is substantially nonhygroscopic.

44. The method of claim 1, wherein the solid form has an X-ray powder diffraction pattern comprising peaks at approximately 14.5° 2θ, 15.7° 2θ, 22.7° 2θ and 29.9° 2θ as shown in FIG. 16, when analyzed using Cu Kα X-ray radiation at 1.54 Å.

45. The method of claim 1, wherein the solid form has an X-ray powder diffraction pattern comprising peaks at approximately 7.2° 2θ, 9.1° 2θ, 14.5° 2θ, 15.7° 2θ, 16.8° 2θ, 18.3° 2θ, 21.9° 2θ, 22.7° 2θ, 29.9° 2θ and 36.9° 2θ as shown in FIG. 16, when analyzed using Cu Kα X-ray radiation at 1.54 Å.

46. The method of claim 44, wherein the solid form has a differential scanning calorimetry plot comprising an endothermic event with an onset temperature of approximately 267° C., when heated from approximately 25° C. to approximately 300° C.

47. The method of claim 44, wherein the solid form is hydrated.

48. The method of claim 1, wherein two or more of the solid forms are administered.

49. The method of claim 1, wherein a pharmaceutical composition comprising the solid form and a pharmaceutical acceptable carrier, diluent or excipient is administered.

50. The method of claim 49, wherein the composition is formulated for oral, parenteral, or intravenous administration.

51. The method of claim 49, wherein the composition is formulated as a single unit dosage form.

52. The method of claim 51, wherein the dosage form is a tablet or capsule.

53. The method of claim 1, further comprising administering a second active agent.

* * * * *